(12) United States Patent (10) Patent No.: US 9,103,784 B1
Sivasankar et al. (45) Date of Patent: Aug. 11, 2015

(54) FLUORESCENCE AXIAL LOCALIZATION WITH NANOMETER ACCURACY AND PRECISION

(71) Applicant: IOWA STATE UNIVERSITY RESEARCH FOUNDATION, INC., Ames, IA (US)

(72) Inventors: Sanjeevi Sivasankar, Ames, IA (US); Hui Li, SuZhou (CN); Chi-Fu Yen, Ames, IA (US)

(73) Assignee: IOWA STATE UNIVERSITY RESEARCH FOUNDATION, INC., Ames, IA (US)

( * ) Notice: Subject to any disclaimer, the term of this patent is extended or adjusted under 35 U.S.C. 154(b) by 0 days.

(21) Appl. No.: 14/081,522

(22) Filed: Nov. 15, 2013

Related U.S. Application Data

(60) Provisional application No. 61/796,641, filed on Nov. 16, 2012.

(51) Int. Cl.
*G01J 1/58* (2006.01)
*G01N 21/64* (2006.01)
*G01B 11/14* (2006.01)

(52) U.S. Cl.
CPC ............ *G01N 21/6404* (2013.01); *G01B 11/14* (2013.01)

(58) Field of Classification Search
CPC .................................................. G01N 21/6428
USPC ....................................................... 250/459.1
See application file for complete search history.

(56) References Cited

U.S. PATENT DOCUMENTS

| 8,212,866 B2 | 7/2012 | Lemmer et al. |
| 2009/0237501 A1 | 9/2009 | Lemmer et al. |
| 2010/0218287 A1* | 8/2010 | Nakata et al. ............... 850/6 |

FOREIGN PATENT DOCUMENTS

| WO | 2009115244 | 9/2009 |
| WO | 2009146016 | 12/2009 |

OTHER PUBLICATIONS

Aguet, F., et al., "A maximum-likelihood formalism for sub-resolution axial localization of fluorescent nanoparticles", Optics Express, vol. 13, No. 26, pp. 10503-10522. Dec. 26, 2005.
Davis, Brynmor J., et al., "4Pi spectral self-interference microscopy", J. Opt. Soc. Am. A, vol. 24, No. 12, pp. 3762-3771. Dec. 31, 2007.
Quirin, Sean, et al., "Optimal 3D single-molecule localization for superresolution microscopy with aberrations and engineered point spread functions", PNAS, vol. 109, No. 3, pp. 675-679. Jan. 17, 2012.
Shtengel, Gleb, et al., "Interferometric fluorescent super-resolution microscopy resolves 3D cellular ultrastructure", PNAS, vol. 106, No. 9, pp. 3125-3130. Mar. 3, 2009.
Yen, Chi-Fen, "Standing Wave Axial Nanometry (SWAN)", presentation Jun. 8, 2012.

(Continued)

*Primary Examiner* — David Porta
*Assistant Examiner* — Hugh H Maupin
(74) *Attorney, Agent, or Firm* — McKee, Voorhees & Sease, PLC

(57) ABSTRACT

We describe a new technique, standing wave axial nanometry (SWAN), to image the axial location of a single nanoscale fluorescent object with sub-nanometer accuracy and 3.7 nm precision. A standing wave, generated by positing an atomic force microscope tip over a focused laser beam, is used to excite fluorescence; axial position is determined from the phase of the mission intensity.

24 Claims, 37 Drawing Sheets

PRINCIPLE OF SWAN

(56) References Cited

OTHER PUBLICATIONS

Yen, Chi-Fen, "Fluorescence Axial Locational with Scanned Standing-Wave (FALSSW)", presentation Nov. 17, 2011.

"Fluorescence Axial Localization with Nanometer Accuracy and Precision", Abstract, Jul. 26-27, 2012 at 2nd Midwest Single Molec Workshop.

Li, Hui, et al., "Fluorescence Axial Localization with Nanometer Accuracy and Precision", NANO Lett. 2012, 12, pp. 3731-3735 (American Chemical Society).

Supporting information for Li, Hui, et al., "Fluorescence Axial Localization with Nanometer Accuracy and Precision", NANO Lett. 2012, 12, pp. 3731-3735 (American Chemical Society).

Yen, Chi-Fu, et al., Li, "Fluorescence Axial Localization with Nanometer Accuracy and Precision", poster presentation, Jul. 26-27, 2012, 2nd Midwest Single Molecule Workshop.

Huang, Bo, et al., "Super resolution fluorescence microscopy", Annu Rev Biochem. 2009; 78: pp. 993-1016. Dec. 31, 2009.

Chi, Kelly Rae, "Super-resolution microscopy: breaking the limits", Nature Methods, vol. 6, No. 1, pp. 15-18. Jan. 31, 2009.

Rief, Matthias, et al., "Single Molecule Force Spectroscopy on Polysaccharides by Atomic Force Microscopy", Science, vol. 275, pp. 1295-1297. Feb. 28, 1997.

* cited by examiner

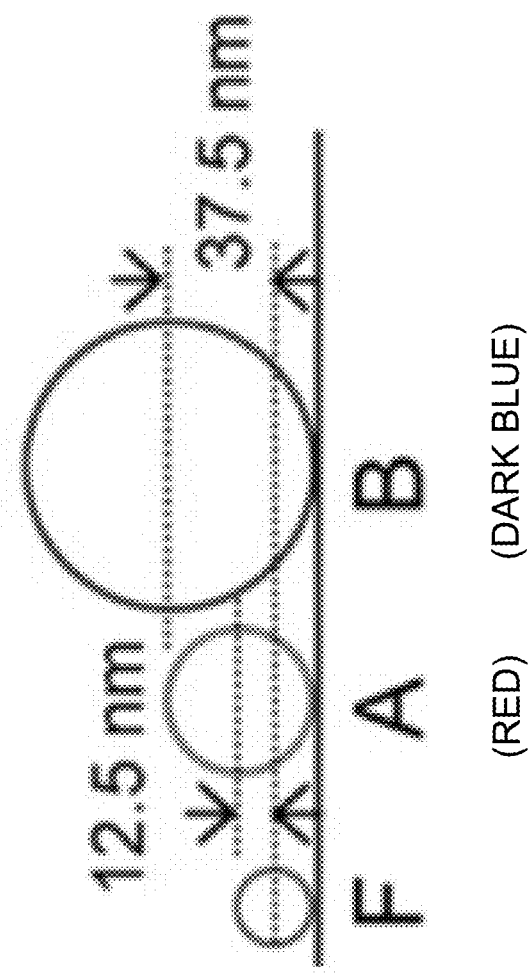

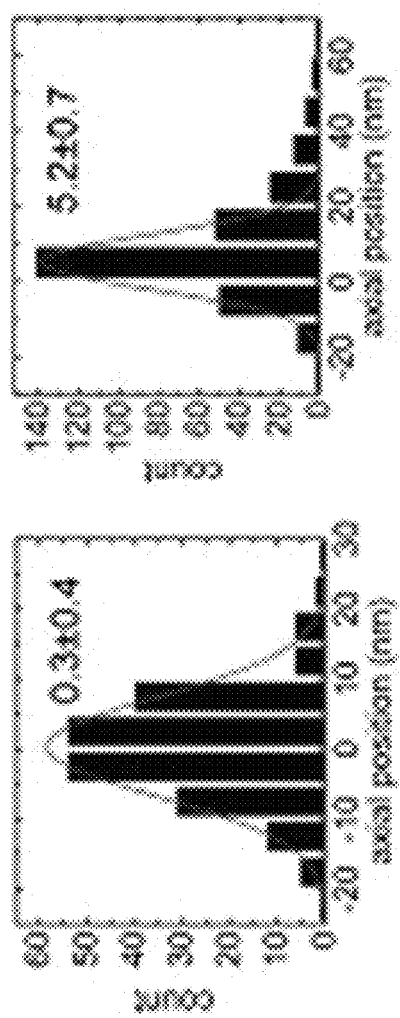

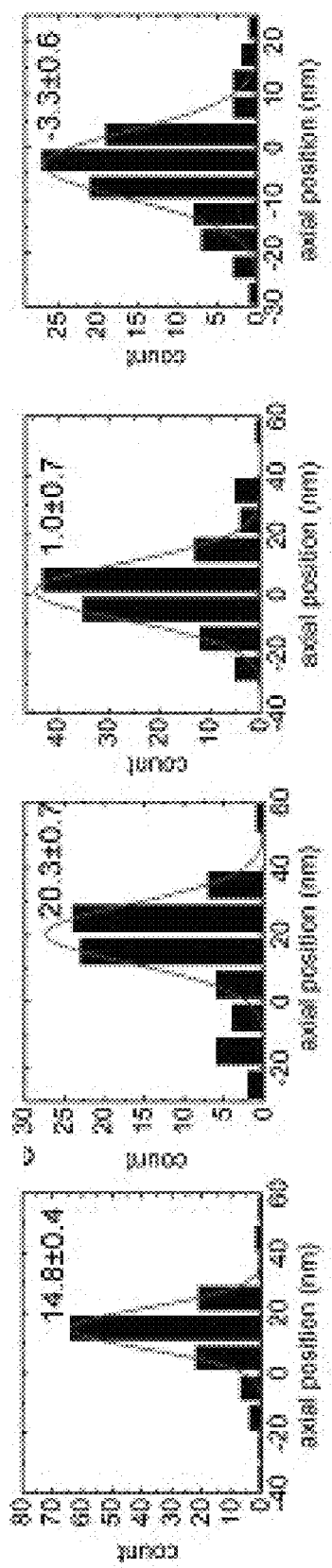

PRINCIPLE OF SWAN

FINITE DIFFERENCE TIME DOMAIN (FDTD)
SIMULATIONS OF STANDING WAVE

PHASE OF STANDING WAVE CHANGES
WITH HEIGHT

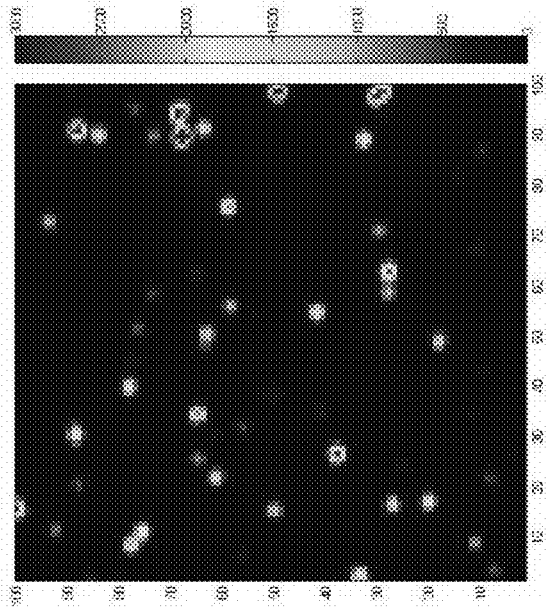
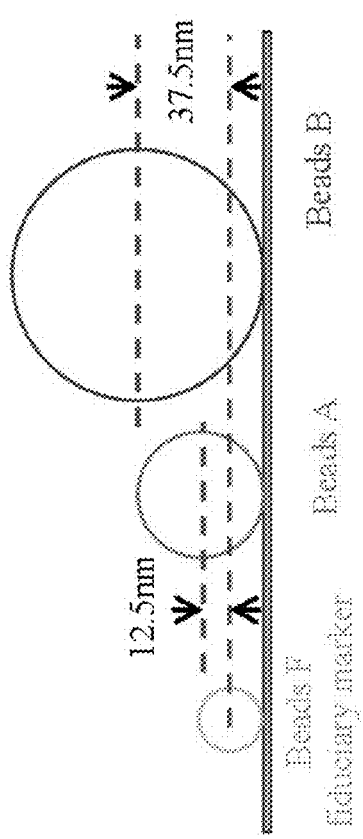
CALIBRATION OF SWAN
FIGURE 15A
BRATION OF SWAN CALI
FIGURE 15B

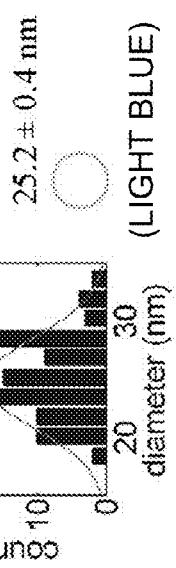
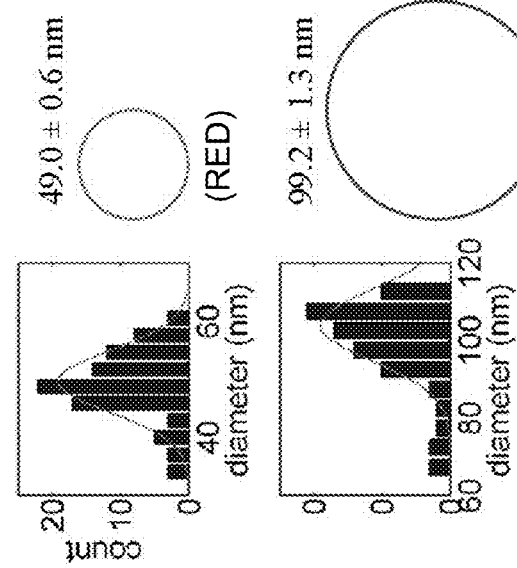
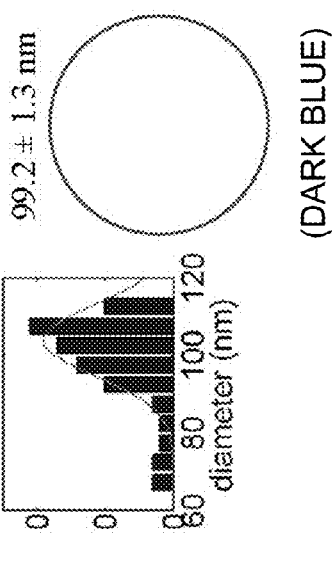
FIGURE 16C
FIGURE 16D
FIGURE 16E
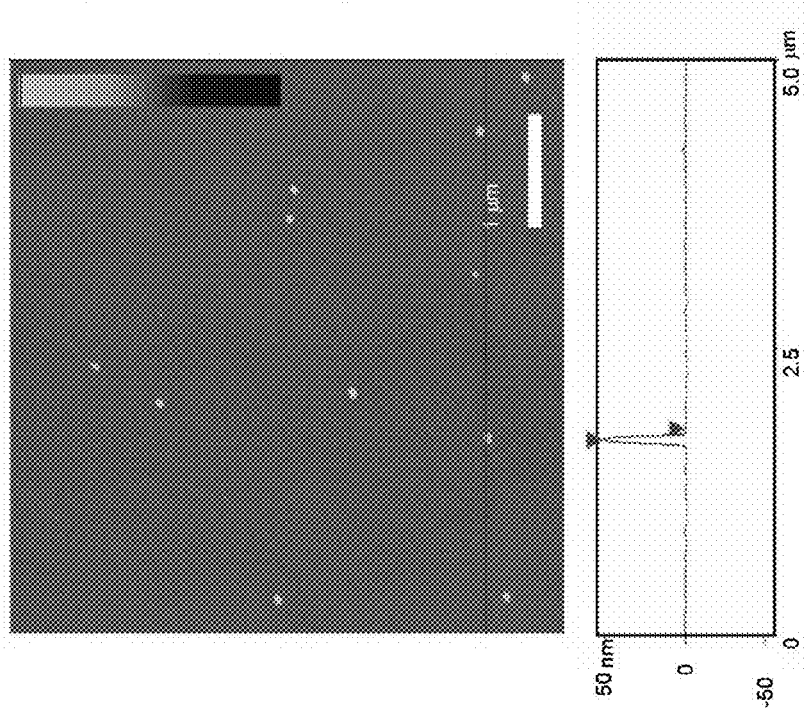
FIGURE 16A
AFM MEASUREMENT OF NANOSPHERES HEIGHT
FIGURE 16B

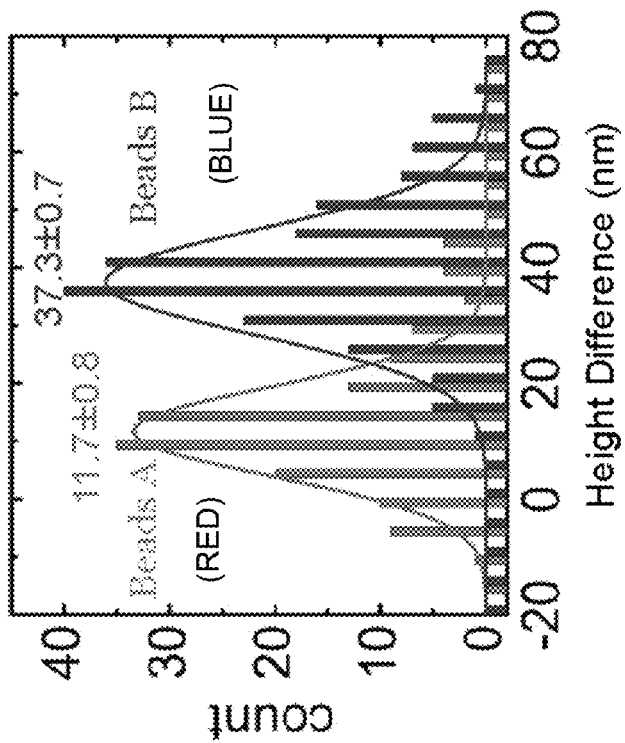
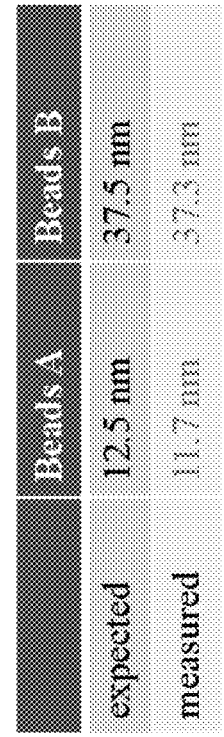
FIGURE 17C
ACCURACY OF SWAN
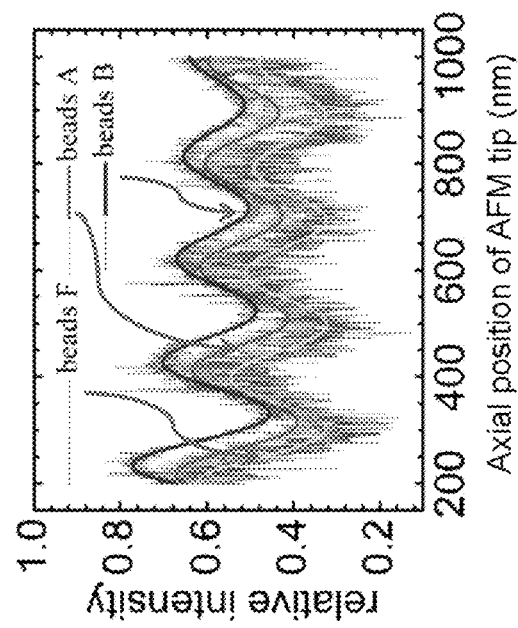
FIGURE 17A
FIGURE 17B

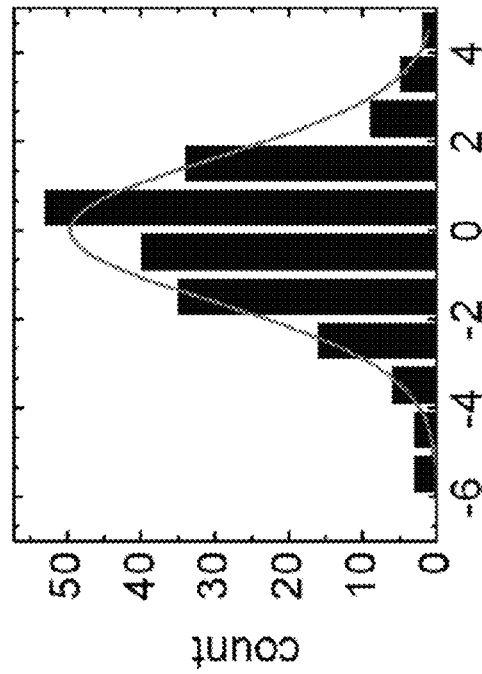
FIGURE 18C
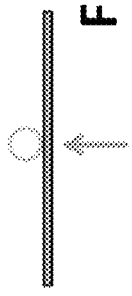
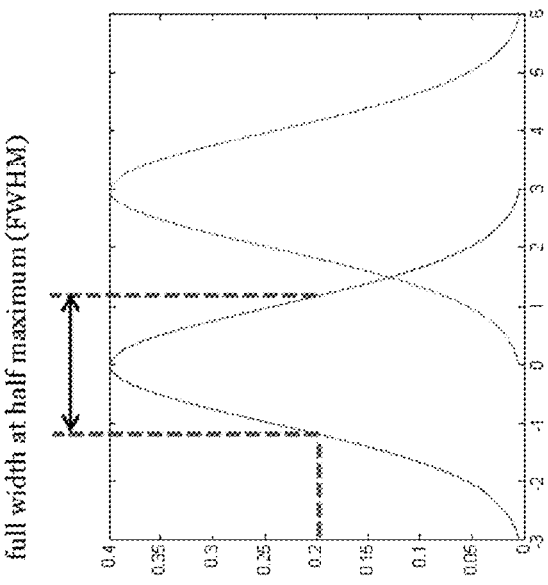
PRECISION OF SWAN
FIGURE 18B
FIGURE 18A ORIENTATION OF IMMOBILIZED dsNDA MEASURED USING SWAN dsDNA OF THREE LENGTHS WERE MEASURED MEASURED HEIGHT OF dsDNA MEASURING THE HEIGHT OF ssDNA and NONSPECIFICALLY ADSORBED dsDNA

FLUORESCENCE AXIAL LOCALIZATION WITH NANOMETER ACCURACY AND PRECISION

CROSS-REFERENCE TO RELATED APPLICATIONS

This application claims priority under 35 U.S.C. §119 to provisional application Ser. No. 61/796,641 filed Nov. 16, 2012, herein incorporated by reference in its entirety.

BACKGROUND OF THE INVENTION

1. Field of the Invention

The present invention relates to microscopy and, in particular, to apparatus, methods, and systems for resolving axial position of nanoscale objects, including but not limited to single molecules or other nanoscale structures.

We disclose a new technique, sometimes called standing wave axial nanometry (SWAN), to determine the axial location of single nanoscale fluorescent objects with sub-nm accuracy and 3.7 nanometer (nm) precision. A standing-wave excitation pattern is generated by positioning an Atomic Force Microscope (AFM) tip or other reflecting surface (e.g. mirror) over a focused laser beam. A fluorescent nanoparticle or a single fluorescent molecule is positioned within the standing-wave and its emission phase difference is used to measure its location along the optical axis. SWAN has an axial precision and localization accuracy that is superior to all previous optical methods. Unlike other approaches, SWAN does not require custom optics or specially engineered substrates, which makes it easy to use with biological samples and live cells. SWAN can be easily integrated with other super-resolution and super-accuracy techniques to image with nanometer resolution along the lateral and axial directions. Moreover, unlike most interference based techniques, where the interference pattern repeats itself and limits the working range on the order of 250 nm, successive periods can be distinguished in SWAN which extends the working distance of this technique. Another unique advantage of SWAN is that it can be used to determine the axial position of molecules in single molecule AFM force measurements and in Single Molecule Cut and Paste applications for the bottom-up assembly of nanostructures.

Unraveling the conformation and function of biomolecules at the nanometer scale requires localizing single molecules with high accuracy and measuring distances between them with high resolution. While single fluorescent dyes can be localized with nm accuracy in the lateral direction, improving resolutions along the optical axis is more challenging.

Here we describe a new technique standing wave axial nanometry (SWAN), to image the axial location of a single nanoscale fluorescent object with sub-nm accuracy and 3.7 nm precision. A standing wave, generated by positioning an Atomic Force Microscope (AFM) tip or other reflecting surface over a focused laser beam is used to excite fluorescence; axial position is determined from the phase of the emission intensity. We use SWAN to measure the orientation of single DNA molecules of different lengths, grafted on surfaces with different functionalities.

2. Related Art

Fluorescence imaging of nanoscale biological assemblies rely on localizing molecules with high accuracy and measuring distances between them with high resolution. However, the resolution of conventional fluorescence microscopes is limited by the diffraction of light: with a high numerical aperture objective and visible excitation, resolution is about 200 nm in the lateral direction and 500 nm along the optical axis.

A single fluorescent molecule can be localized with nanometer accuracy along the x- and y-axis by determining the centroid of its point spread functions (PSF)[1], a technique known as fluorescence imaging with one nanometer accuracy (FIONA)[2]. This approach has also been used to resolve the lateral separation between two dyes of the same or of different colors within a diffraction-limited spot[3-5]. FIONA has been combined with the stochastic switching of single molecule fluorescence to obtain high-resolution images of microscopic biological objects such as cells, an approach alternatively known as stochastic optical reconstruction microscopy (STORM)[6], photoactivated localization microscopy (PALM)[7], and fluorescence photoactivated localization microscopy (FPALM)[8]. The lateral resolution of fluorescence imaging can also be improved by using stimulated emission depletion (STED) to narrow the effective width of the PSF[9, 10].

Unlike imaging in the x- and y-direction, improving resolution and single molecule localization accuracy along the optical axis is more challenging[11]. In STORM experiments, the z-position of a single fluorophore can be determined with 50 nm resolution using a cylindrical lens to distort the shape of the PSF[12]; resolution can be further improved to 20 nm by sandwiching the sample between two opposing objectives[13]. Better resolution, down to 10 nm, can be achieved using interferometry as demonstrated in interferometric photoactivated localization microscopy (iPALM) and 4Pi-single marker switching microscopy (4Pi-SMS)[14, 15]; this however requires the use of custom optics in a complicated layout for interference detection. Alternatively, fluorescence interference-contrast microscopy (FLIC) has been used to determine the height of dye monolayers with nanometer accuracy[16]; these experiments however require multiple replicas of the sample deposited on patterned silicon oxide surfaces which limits its applicability in single molecule biological imaging. Fluorescence interference has also been used to monitor the movement of single motor proteins on microtubules[17].

Therefore a need for improvement in the art exists.

SUMMARY OF THE INVENTION

The present invention relates to improvements in microscopy. In particular, the present invention relates to improvements in localization of nano-scale objects, including in the axial direction.

One aspect of the invention comprises a method to localize nano-scale structures with higher accuracy and precision in the axial direction. In one form, the methodology takes advantage of the capabilities of an AFM/fluorescence microscope combination. The excitation laser of the fluorescence microscope is operated with the AFM tip in alignment along the optical axis to set up a standing wave of the excitation laser energy between the AFM tip and the sample surface. As will be described in detail later, height or location of a fluorescent object excited by the standing wave can be derived from the phase of its fluorescence emission. The standing wave oscillates at frequency related to the interference between the direct laser energy through the sample surface and its reflection back along the same path from the aligned AFM tip. The phase of the standing wave varies as a function of distance from the sample surface. If a fluorescent object is placed in the standing wave and excited by the standing wave, its fluorescence oscillates with a phase that corresponds to its distance from the sample surface. This allows accurate and precise localization of the object or structures to which such objects are attached. The method can be applied advantageously in a variety of ways. Instead of using the AFM tip as a reflecting surface, a different reflecting surface (e.g. mirror) could be substituted.

In another aspect of the invention, an integrated AFM-FM apparatus can be configured to carry out the SWAN methodology. As will be discussed in more detail below, this can include components to allow data acquisition of intensity of the fluorescence from the fluorescent object in the standing wave, as well as intensity of the excitation source. Another reflecting surface could be substituted for the AFM tip. The methodology could be applied to many microscope types. Examples include, but are not necessarily limited to, confocal, wide-field, TIRF, mulitphoton, and epi-illumination.

Another aspect of the invention is a method to align the AFM tip with the excitation laser along the optical axis of the microscope, and then align the sample along the optical axis. The method first determines, with nanometer precision, the location of the center of the AFM tip. The AFM tip is imaged by precisely moving it through the fixed excitation laser beam and measuring the light reflected off the AFM tip at each location. The center of the tip is determined by finding the centroid of the optical intensity of the reflected light in the image. This allows moving the tip into precise alignment with the excitation beam. The method can also determine the position(s) of target fluorescent molecules(s) or other structures in a sample by similarly scanning the sample through the laser beam. The molecule(s) or structure(s) is/are similarly imaged by measuring fluorescent emissions from the molecules for each scan position. In one example, by fitting each image to a Gaussian function, the intensity peaks are calculated. The peaks are indicative of molecule position to many-times nanoscale precision. Thus, fine alignment between AFM tip and excitation laser is accomplished for setting up the standing wave in SWAN, and also the standing wave and target molecules for axial localization of the target molecules with SWAN. An alternative to use of the AFM tip as a reflective surface is use of an actual mirror or analogous component that is scannable in nanoscale fashion like the AFM tip. Other reflecting surfaces could be substituted for the AFM tip.

As can be appreciated, potential applications are many. A few include, but are not limited to, the following.

Fluorescence microscopy is widely used for noninvasive, time-resolved imaging of the structure, function and dynamics of single biomolecules. These applications rely on localizing molecules with high accuracy and measuring distances between them with high resolution. However, the resolution of conventional fluorescence microscopes is limited by the diffraction of light to about 200 nm in the lateral direction and 500 nm along the optical axis; improving the resolution and localization accuracy of fluorescence techniques is therefore a very active area of research. Many "super resolution microscopy" techniques have been developed to localize single fluorescent dye with nm accuracy in the lateral direction; however, improving resolution along the optical axis is more challenging. Here, we describe a new localization method, based on standing wave excitation and fluorescence readout, to determine axial location with sub-nanometer accuracy and 3.7 nanometer resolution. Our technique has potential applications, including but not limited to, in 1. Life science research: Imaging healthy and diseased cells with high resolution. Determining the structure and dynamics of biological molecules such as DNA and proteins. Determining the interaction of biomolecules with receptors and toxins in living cells.

2. Drug discovery: Direct observation of targeted drug delivery and drug interactions in vitro, in live cells and tissue. This will enable rational design of better pharmaceutical products
3. Nanoscience and Nanotechnology: Characterization of the optical properties of nanoscale materials like semiconductor nanocrystals, nanotubes and nanowires. This will enable development of new technologies for energy harvesting and biomedical diagnostics.
4. Material science: Characterization of materials with novel optical properties.
5. Optical MEMS industry: Design of more efficient Optical MEMS devices by imaging them with nm accuracy and precision.

A goal, object, feature, or aspect of the present invention is to provide for axial localization with nanometer accuracy and precision and without costly and complex components. Another goal, object, feature, or aspect of the invention is accurate and precise axial localization in a wide variety of beneficial applications. Further objects, features, aspects, and advantages of the present invention will become apparent with reference to the accompanying specification and claims.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 1B is a color photograph.

FIGS. 2A-D are diagrammatic illustrations and charts illustrating how a SWAN system can be calibrated for use. FIG. 2B is a color photograph of recorded measurements.

FIGS. 3A-G are diagrams and charts illustrating application of SWAN to estimate orientation of nanoscale structures in three dimensional space.

FIG. 6A is a color photograph.

FIG. 11A includes a color photograph.

FIG. 14B includes color photographs of images and recorded measurements.

FIG. 15A diagrammatically illustrates in greatly enlarged scale calibration objects of known size used in one method of calibration of the invention.

FIG. 15B is a fluorescent image at noted scale related to a set of distributed calibration objects. FIG. 15B is a color photograph.

FIGS. 16A and 16B are similar to FIGS. 6A and 6B with additional illustrative information relative to calibration using objects of known size. FIG. 16A includes a color photograph.

FIGS. 16C-E are illustrative diagrams.

FIGS. 17A-17C are graphic illustrations of showing a precision of the methodology of the present invention. FIG. 17A is a color photograph of recorded measurements.

FIGS. 18A-C are graphs and diagrams illustrating precision of the invention.

The following is incorporated by reference herein, Li, H., Yen, C., Sivasankar, S., NANO LETT. 2012, 12, 3731-3735 (including Supporting Information). [Retrieved from Internet at http://pubs.acs.org/doi/suppl/10.1021/nl301542c], in particular nl301542c_si_001.pdf, incorporated by reference herein.

DETAILED DESCRIPTION OF EXEMPLARY EMBODIMENTS

Overview

For a better understanding of the invention, several exemplary embodiments which illustrate aspects of the invention will now be described in detail. It is to be understood that these are but several examples of forms the invention can take and are neither inclusive nor exclusive. Variations obvious to those skilled in the art will be included within these examples. But the invention and its aspects can take many other and different forms of embodiments.

Example of Apparatus

Figure 4:
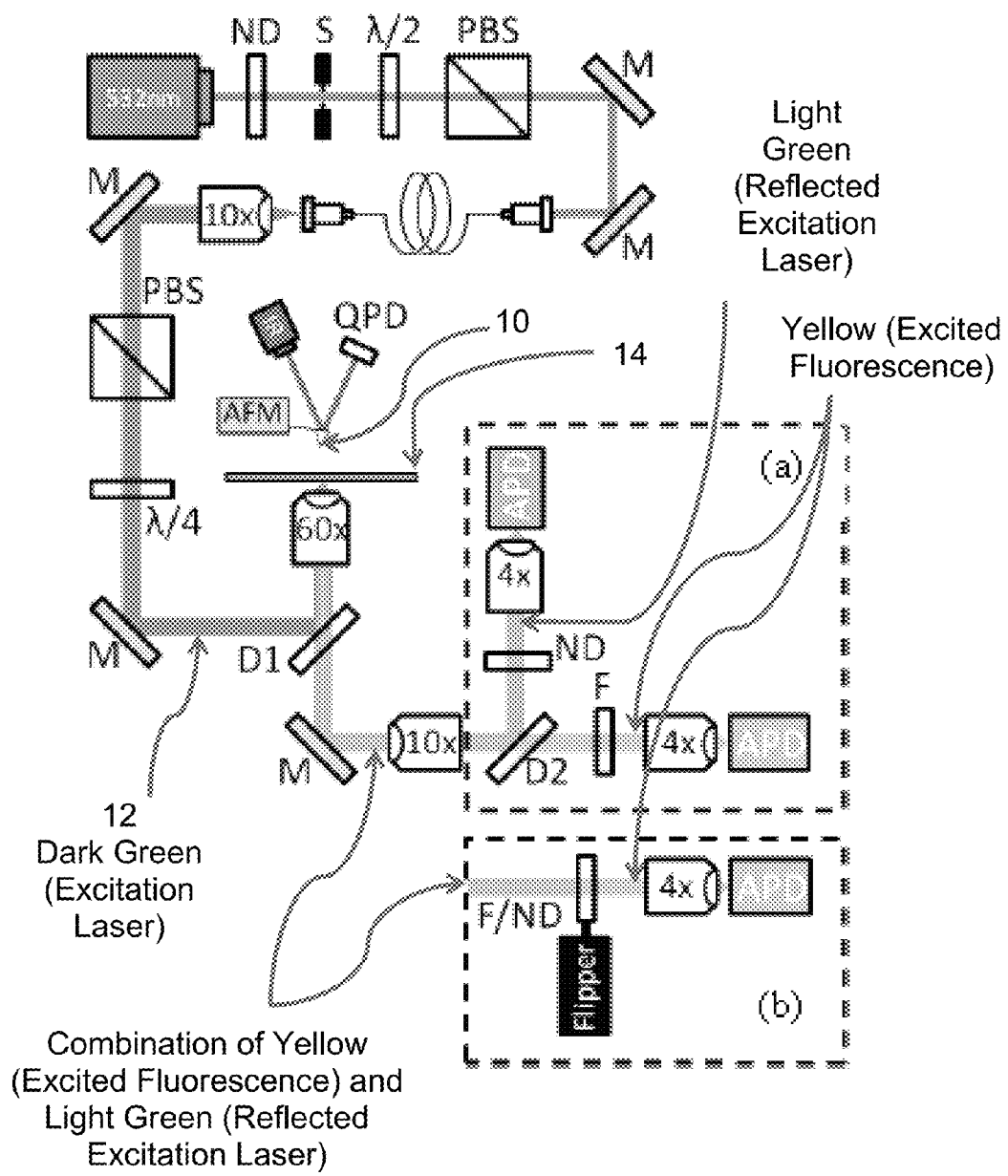
FIG. 4 is a diagrammatic illustration of a combined AFM/fluorescence microscope system for use with SWAN.

An example of an apparatus for SWAN is shown at FIG. 4.

At a general level, the apparatus is a combination of a confocal fluorescence microscope and an AFM microscope. This includes components for AFM functions as well as for fluorescent measurements. Such systems are commercially available or can be assembled for operation by those skilled in the art.

Such systems would include a user interface, processor(s), and actuators to perform AFM/fluorescence microscopy functions, including nanoscale adjustment of AFM tip/scanner and stage(s) in three dimensional space an AFM sub-system with conventional components including tip 10. It also includes one or more lasers and appropriate optics (see FIG. 4) to direct each to a common optical path to the microscope objective. This allows a selected single laser to be utilized in certain applications, or plural lasers to be either sequentially or simultaneously used.

Another sub-system includes optics to deliver light returned through the objective by reflection or fluorescence from excitement by the laser at the AFM tip or sample. The sub-system can provide different options for recording such information (e.g. photodiodes, imagers/camera, etc.).

In particular it is noted that the SWAN set up of FIG. 4 allows electric field intensity measurements to be made independently of either excitation laser wavelengths or fluorescence wavelengths from fluorescent objects excited by the excitation laser.

Example Methods of Use

Following is a description of the high level concepts of SWAN as well as its implement and validation.

By reference to FIGS. 1A-D and 2-5, here we describe a new localization method with an axial resolution superior to previous techniques to determine the z-position of a single nanoscale fluorescent object with sub-nanometer accuracy. Our technique, called standing wave axial nanometry (SWAN), utilizes a commercial atomic force microscope (AFM) mounted on a single molecule confocal microscope[18]. A standing wave excitation pattern is generated between an AFM tip 10 and the microscope specimen surface 14 by positioning the AFM tip[10] over a focused laser beam[12]. A fluorescent object[20] is positioned within the standing wave and its fluorescence phase difference is used to measure the molecule's axial location ($Z_{mol}$).

As a proof of principle, we use SWAN to measure the orientation of single-stranded DNA (ssDNA) and double-stranded DNA (dsDNA) of different lengths, grafted on surfaces with different functionalities. The conformation of immobilized DNA affects surface hybridization efficiency[19] and critically impacts techniques such as DNA microarrays and gene sequencing. Previously, ensemble methods such as ellipsometry[20], surface plasmon resonance[21], and fluorescence self-interference[22] have been used to characterize the orientation of DNA bound to surfaces at high densities, where steric effects from neighboring molecules influence conformation. However, the orientation of single, tethered DNA has not been measured. Using SWAN, we show that dsDNA of different lengths, grafted using polymer tethers, are oriented at an average tilt of 30° with respect to the surface. On the other hand, dsDNAs adsorbed nonspecifically to a positively charged surface lie flat. Finally, a single-stranded G-quadruplex sequence, folds into a structure where its 5' and 3' ends are adjacent to each other.

Principle of SWAN.

Figure 1A:
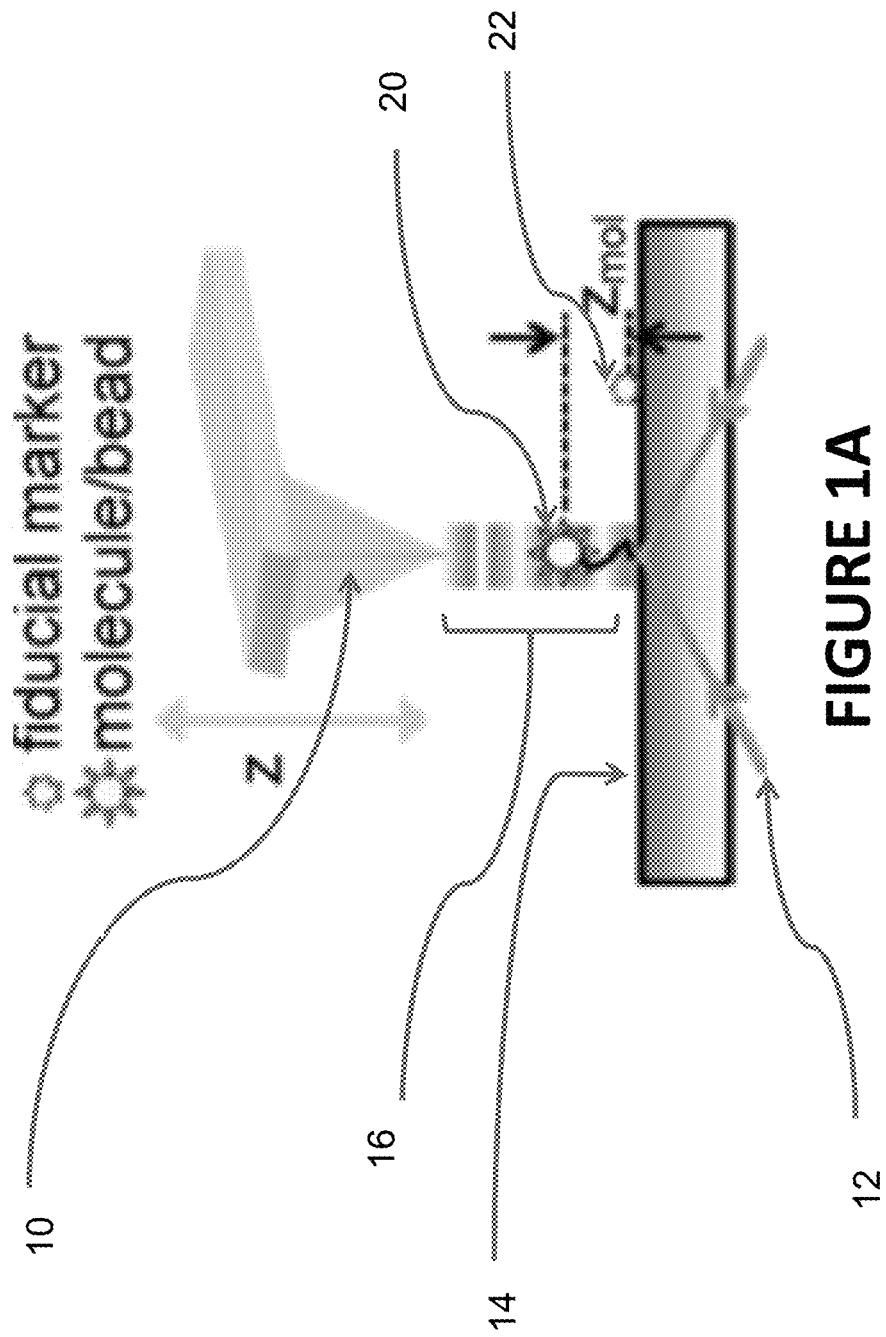
FIGS. 1A-D are illustrations of basic principles of SWAN according to one exemplary embodiment of the present invention.
Figure 13A:
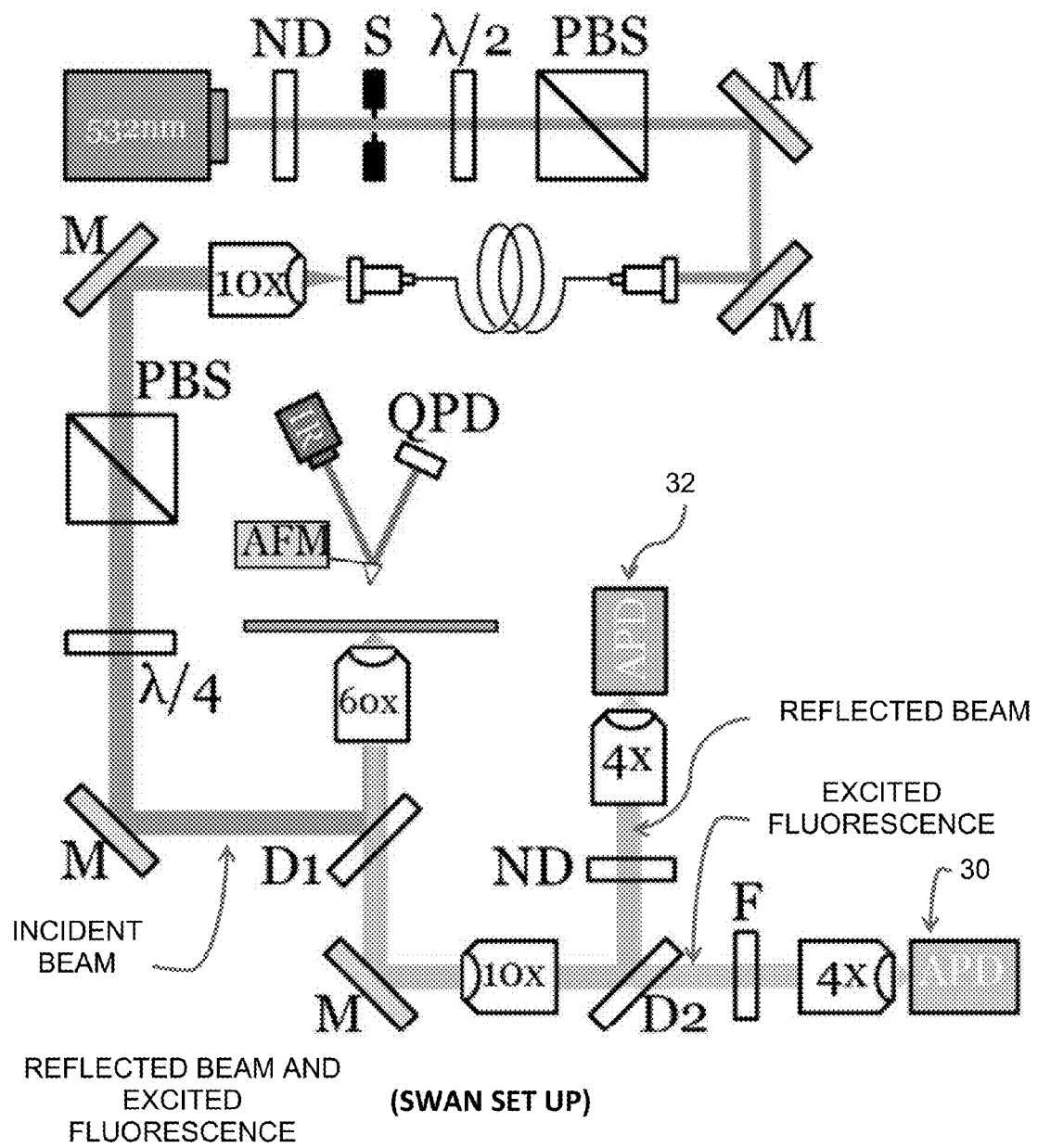
FIG. 13A is similar to FIG. 4.

In SWAN, an AFM tip[10], which serves as a reflecting surface or mirror, is positioned over the focused laser beam[12] of a confocal microscope (see also Supporting Information infra, and FIG. 13A). Interference between the incident beam and the beam reflected off the AFM tip, results in a standing wave[20] between the tip[10] and surface[14] (FIG. 1A). As the tip is translated in the z-direction, the fluorescence emitted by a fluorophore[20] positioned within the standing wave oscillates with a phase that corresponds to its distance from the surface. Axial location ($Z_{mol}$) of the fluorophore[20] can be measured from the phase difference relative to a fiduciary marker[22] (FIG. 1A).

As the AFM tip[10] moves by a distance Z along the optical axis, the phase difference between the incident and reflected beams at a height $Z_{mol}$ above the surface is given by:

$$\phi = \frac{2\pi \times 2 \times (Z + Z_0 - Z_{mol})}{\frac{\lambda_{laser}}{n}} \quad (1)$$

where $Z_0$ is the initial position of the AFM tip, $\lambda_{laser}$ is the wavelength of the excitation laser and n is the refractive index of the medium. The excitation intensity of the incident beam along the optical axis corresponds to the shape of the PSF and can be described by a power law[23]. Ignoring higher order terms, the excitation intensity at $Z_{mol}$ due to interference of the incident and reflected beams is given by:

$$1 = A^2 + \frac{B^2}{1 + CZ^2} + 2A\frac{B}{\sqrt{1 + CZ^2}}\cos(\phi) \quad (2)$$

where A and B are the amplitudes of the incident and reflected beams and C is the fitted amplitude decay that is related to the focal depth of the microscope[23]. Since the emitted fluorescence intensity is proportional to the excitation intensity, the height of a fluorescent object located at $Z_{mol}$ can be determined by fitting its fluorescence emission to eq 2.

Figure 1B:
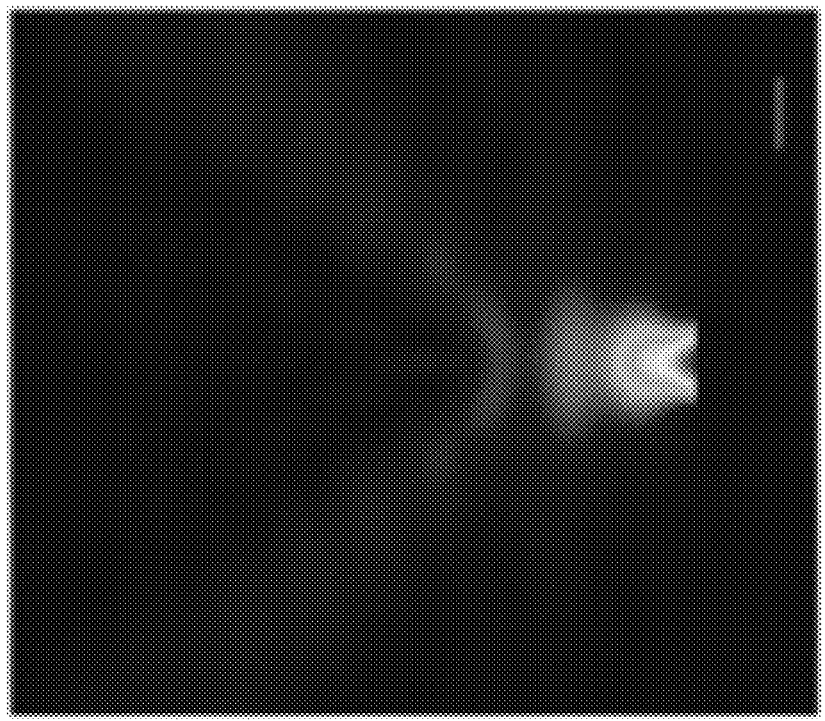
Figure 1C:
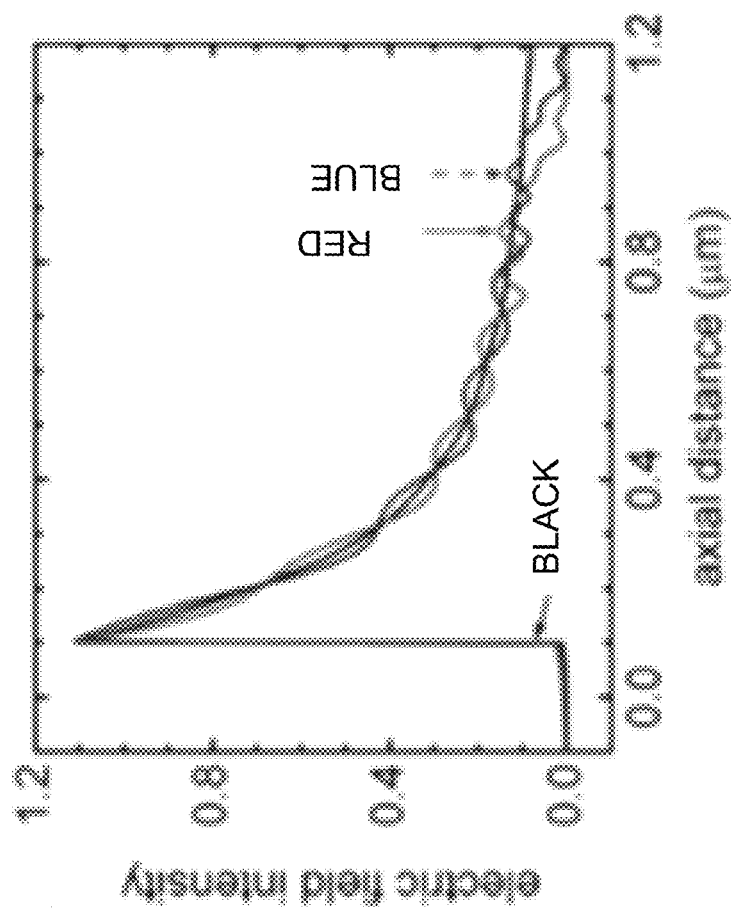
Figure 1D:
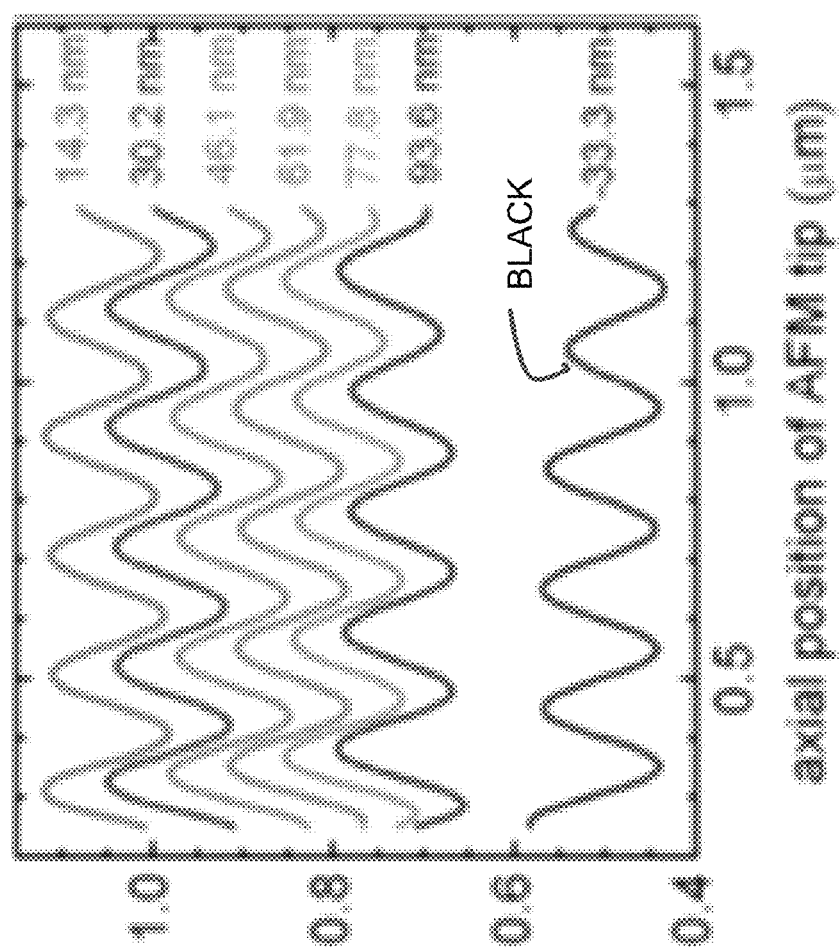

We used finite difference time domain (FDTD) simulations to calculate the electric field intensity distribution when the AFM tip was located over a focused excitation laser (see Supporting Information section below). The simulations show periodic oscillations in the electric field in the gap between the AFM tip[10] and coverslip[14], corresponding to a standing wave generated due to the interference between the incident excitation and the beam reflected off the tip (FIG. 1B). The electric field intensity along the optical axis is plotted in FIG. 1C. Without a tip, the intensity decays rapidly in the axial direction corresponding to the shape of the PSF. When the AFM tip is present, periodic oscillations of the electric field are superimposed on this decay (FIG. 1C). By changing the distance between the tip and surface, the phase of the oscillation can be modulated: for instance, the phase is reversed when a tip 0.75 μm from the coverslip is relocated 0.85 μm away from the surface (FIG. 1C). We also monitored the electric field intensity at six positions along the optical axis while the tip was translated from 250 nm to 1.3 μm in 13 nm steps (FIG. 1D). As the distance from the surface increased, the average intensity decreases. However, the field at the six positions oscillate with different phases (FIG. 1D).

Figure 5:
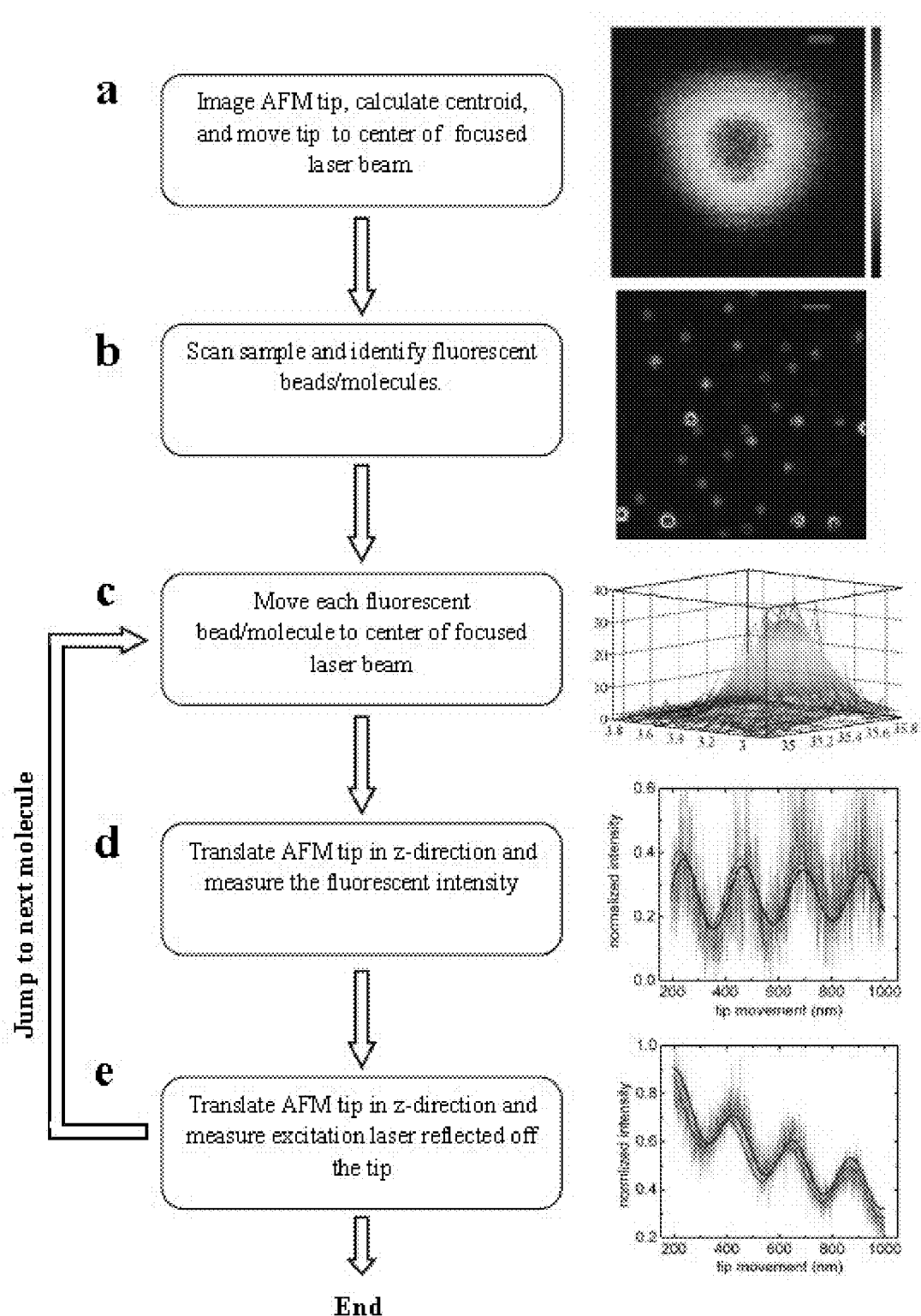
FIG. 5 is a flow chart of an exemplary methodology according to an aspect of the invention with color photographs of images and recorded measurements.

In order to excite a fluorophore using the standing wave, the fluorophore and AFM tip were aligned along the microscope's optical axis (see Supporting Information section and FIG. 5). To ensure that the tip does not contact the molecule during the experiment, the AFM tip was held at a minimum $Z_0$ of 200 nm above the surface. The tip was translated in the axial direction from 200 to 1200 nm, while monitoring fluorescence emitted by the molecule. We determined the absolute tip-coverslip distance by measuring the interference of the excitation laser reflected off the coverslip and AFM tip and also by comparing the fluorescence phase difference of the dye to fiduciary markers bound to the coverslip (Supporting Information section and FIG. 5).

FIGS. 1A-D.

Schematic and validation of SWAN experiment. FIG. 1A: Schematic of experiment. A standing wave[16], generated by positioning an atomic force microscope tip[10] over a focused laser beam[12], is used to excite a nanoscale fluorescent object[20]. Its axial position is determined from the phase difference of the fluorescence emission relative to a fiducial marker[22]. FIG. 1B: FDTD simulations show periodic oscillations in the electrical field intensity in the 0.75 μm gap between a silicon tip and coverslip. Scale bar=200 nm. FIG. 1C: Electric field intensity along the axial direction under three conditions: black, without tip; red, with tip 0.75 μm away from the surface (indicated by the red arrow); and blue, with tip 0.85 μm away from the surface (indicated by the blue arrow). Without a tip, the intensity along the optical axis decays rapidly due to the shape of the PSF. When an AFM tip is present, periodic oscillations in the electric field intensity are measured. Black arrow corresponds to location of coverslip surface which is also the position of laser focus. FIG. 1D: Electric field intensities, monitored at six positions (see curve labels 14.3 nm, 30.2 nm, etc.) along the optical axis, as the AFM tip moves from 250 nm to 1.3 μm. The intensities oscillate with different phases. The black curve shows the intensity below the coverslip (magnified 10 times for clarity). Oscillations in the black curve, which result from the interference of light reflected from the coverslip and AFM tip, are used to determine the coverslip position.

SWAN Calibration.

We determined the accuracy of SWAN by measuring the radius of polystyrene nanospheres of different sizes, uniformly loaded with fluorescent dyes (see NANO LETT. 2012, 12, 3731-3734 and supporting material). Because each nanosphere contains a large number of dyes, SWAN measures the average height of all the fluorophores within a single nanosphere, that is, the nanosphere radius. We measured fluorescent nanospheres with manufacturer specified diameters of 50 nm (Bead A—also labeled in FIG. 2A "RED") and 100 nm (Bead B—also labeled in FIG. 2A "DARK BLUE") relative to fiducial beads (Bead F) with a diameter of 25 nm (FIG. 2A). We also verified the size of the nanospheres using tapping-mode AFM imaging (well-known in the art); measured diameters were consistent with the manufacturer specified values. Average bead diameters (mean±standard error of mean) of 25.2±0.4 nm, 49.0±0.6 nm, and 99.2±1.3 nm were measured for Beads F (97 beads), Beads A (90 beads), and Beads B (85 beads), respectively (see also Supporting Information section, infra, and FIGS. 6A-E). Histograms of the measured diameters were fit to a Gaussian function to estimate bead polydispersity; fits to Beads F, Beads A, and Beads B had a full width at half maxima (FWHM) of 7.5, 10.3, and 18.0 nm, respectively (see Supporting Information, infra and FIGS. 6A-E).

Figure 2B:
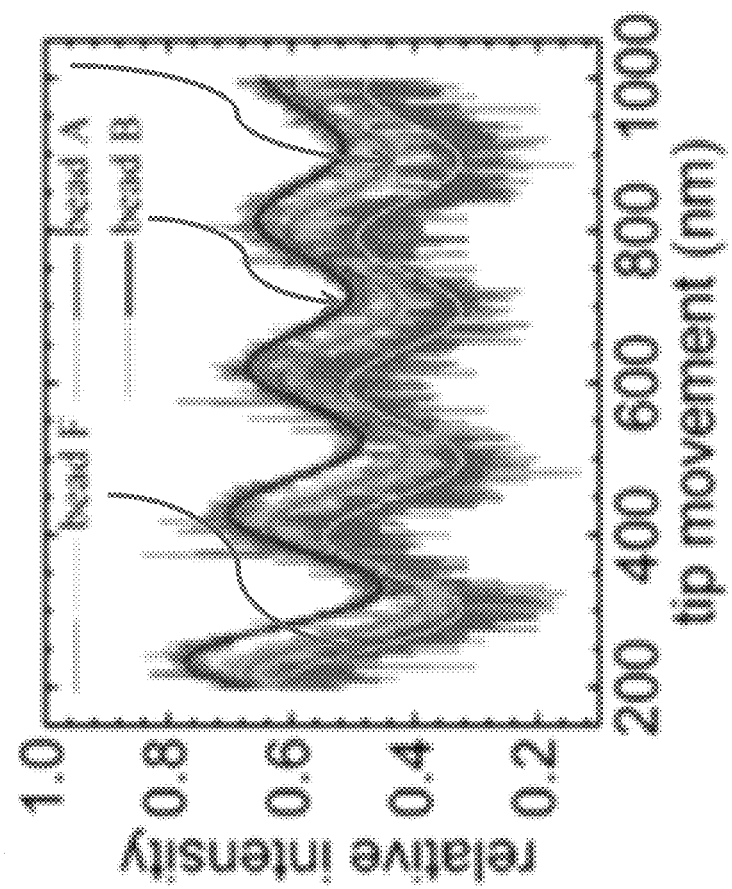
Figure 2C:
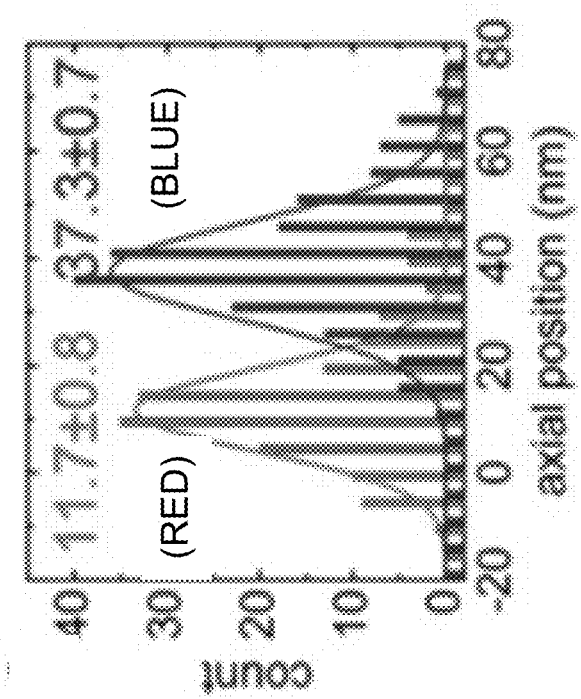

Typical SWAN data traces along with their fits to eq 2 are shown in FIG. 2B. Relative to the fiducial beads, we expected to measure a height of 12.5 nm for Bead A and 37.5 nm for Bead B (FIG. 2A). In close agreement, we measured relative radii (mean±standard error of mean) of 11.7±0.8 nm for Beads A (181 beads) and 37.3±0.7 nm for Beads B (178 beads) relative to Beads F (181 beads) (FIG. 2C). This demonstrates that the accuracy of SWAN is less than 1 nm. It should be noted that increasing the sample size (i.e., number of nanospheres) will not increase the accuracy of the measurement. The standard deviations of the measured radii were 8.1 and 7.2 nm, respectively; we ascribe this in part to the polydispersity in the measured bead sizes.

To quantify the resolution of SWAN, we measured the height of a single Bead F 100 times. The fluorescence intensity of the bead varied between 50 and 100 kHz and photons were collected for 1 s. To increase the precision of our measurement, we reduced instrumental drift by simultaneously recording the fluorescence intensity and excitation laser interference rather than measuring them sequentially. The measured bead radius had a standard deviation of 1.6 nm (FIG. 2D), which corresponds to an axial resolution of 3.7 nm (FWHM). This resolution is almost three times better than interferometric techniques[14, 15] and more than five times better than optical astigmatism.

FIGS. 2A-D.

Figure 2D:
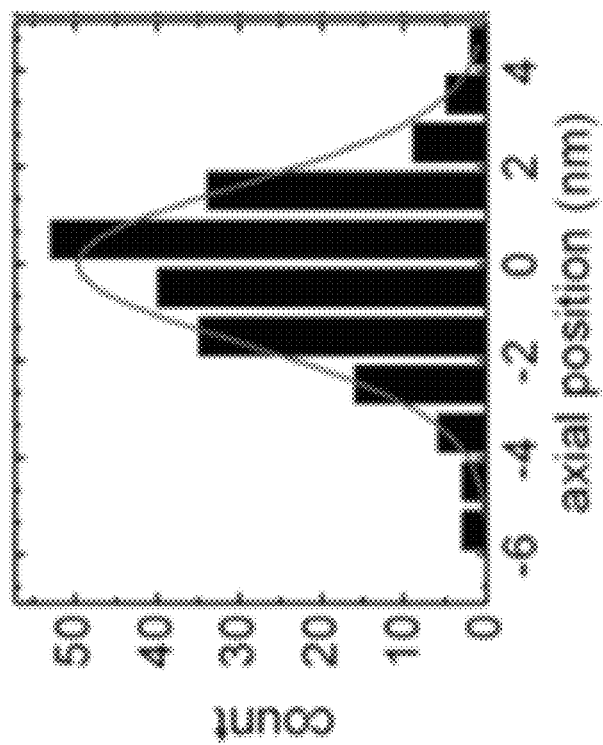

Calibration of SWAN using fluorescent nanospheres. FIG. 2A: Schematic of experiment. The relative radii of 25 nm (Bead A—also labeled "RED") and 50 nm (Bead B—also labeled "DARK BLUE") fluorescent nanospheres were measured relative to 12.5 nm (Bead F) fiducial beads. We expect to measure a relative radii of 12.5 and 37.5 nm for Beads A and B, respectively. FIG. 2B: Typical experimental data traces (thin lines) along with their fits (thick lines) to eq 2. FIG. 2C: Histograms of the measured radii were normally distributed; the peak of a Gaussian fit corresponded to the mean radii while the standard error of mean corresponded to the error. The measured relative radii for Beads A and Beads B were 11.7±0.8 and 37.3±0.7 nm, respectively. FIG. 2D: The axial position of a single Bead F was measured 100 times; the measured values had a standard deviation of 1.6 nm, which corresponds to a localization precision (FWHM) of 3.7 nm.

Measurement of Single DNA Orientation.

Figure 3A:
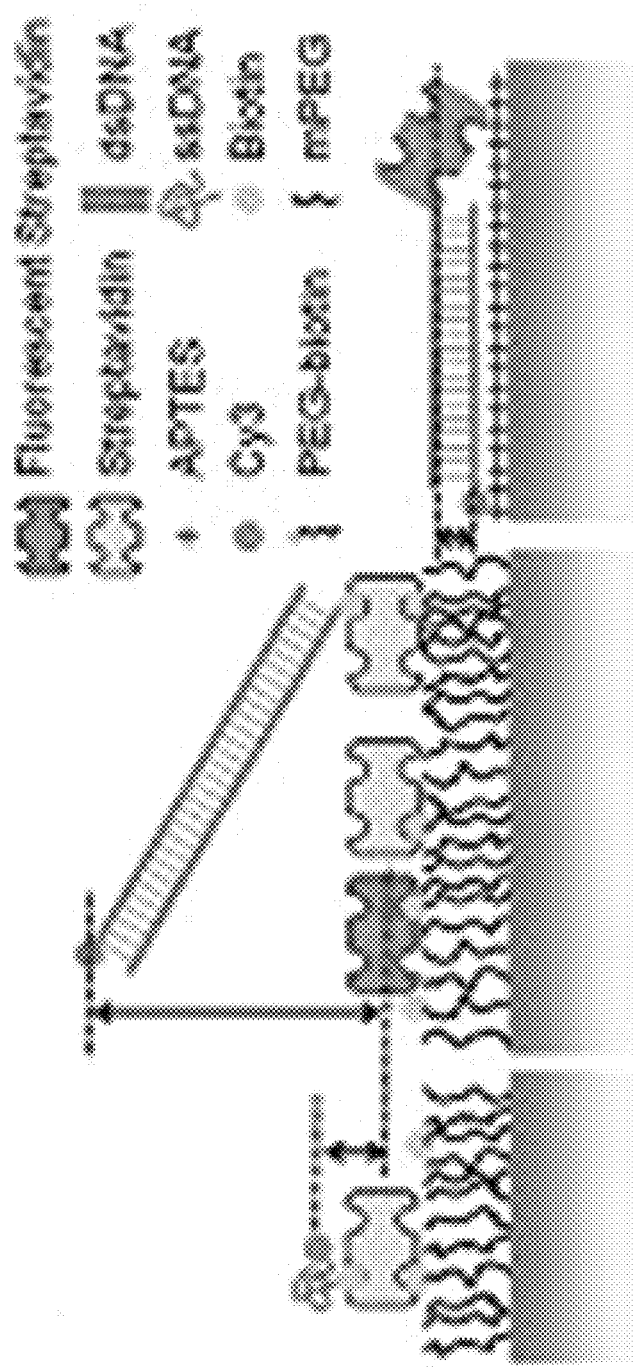

We used SWAN to measure the orientation of ssDNA and dsDNA molecules, labeled with a Cy3 fluorophore at one end and a biotin anchor at the other end. The DNA was tethered on a flexible polyethylene glycol (PEG) cushion decorated with nonfluorescent streptavidin (FIG. 3a, Supporting Information). Average DNA orientation was measured relative to fluorescent Alexa Fluor 555 streptavidin that served as a fiduciary marker (FIG. 3A).

The ssDNA was a G-quadruplex sequence that folds into a four-stranded structure[24] in the presence of Na+; when folded, the Cy3 is located at the same height as fluorescent streptavidin (FIG. 3A). In the presence of Na$^+$, we therefore anticipate measuring a height of 0 nm for the Cy3 relative to the fiducial. Indeed, in 50 mM Na$^+$, we measured a height of 0.3±0.4 nm (FWHM, 16.6 nm) for the ssDNA (FIG. 3B).

We also measured the orientation of 3 dsDNA sequences with lengths of 35 base pairs (bp), 90 bp, and 122 bp. Since the contour lengths of the 35 bp and 90 bp fragments are much smaller than the 50 nm persistence length of dsDNA, these sequences are expected to behave as stiff rods. On the other hand, the 122 bp DNA fragment has a contour length of 41.5 nm that is comparable to the dsDNA persistence length; the end-to-end distance of this sequence was estimated to be 36.5 nm, 12% shorter than the contour length according to worm-like chain model[25]. It is anticipated that the tethered dsDNA freely rotates in the space above streptavidin[22]. Calculations show that under these conditions dsDNA is oriented at an average tilt of 30° with respect to the surface (Supporting Information, FIG. S4). Using SWAN we measured a height of 5.2±0.7 nm (FWHM, 17.2 nm), 14.8±0.4 nm (FWHM, 15.5 nm), and 20.3±0.7 nm (FWHM, 18.1 nm) for the three sequences, corresponding to tilt angles of 26°, 29°, and 34°, respectively (FIGS. 3C-E).

A widely used approach to lay DNA flat on a surface is to adsorb it nonspecifically to a self-assembled monolayer of positively charged aminopropyltriethoxysilane (APTES) (FIG. 3A)[26]. We adsorbed 35 bp dsDNA, 122 bp dsDNA, and fluorescently labeled streptavidin on a freshly prepared APTES surface and used SWAN to measure the difference in height between the dsDNA and fluorescently labeled streptavidin which served as a fiduciary marker. We measured a height of 1.0±0.7 nm (FWHM, 22.6 nm) for 35 bp dsDNA (FIG. 3F) and −3.3±0.6 nm (FWHM, 15.0 nm) for 122 bp dsDNA (FIG. 3G), indicating that both dsDNAs are lying flat on the surface.

FIGS. 3A-G.

Orientation of immobilized DNA molecules measured using SWAN. FIG. 3A: Schematic of the different DNA immobilization strategies used. ssDNA G-quadruplex (left panel) and dsDNA (middle panel) was tethered on a PEG cushion decorated with nonfluorescent streptavidin, via a biotin group. dsDNA (right panel) was also nonspecifically adsorbed to a self-assembled monolayer of positively charged silanes. Fluorescently labeled streptavidin served as a fiducial marker in all the experiments. FIG. 3B: The measured height of 35 base ssDNA G-quadruplex sequence corresponds to a structure where the 5' and 3' ends are adjacent to each other. Histogram of measured heights for FIG. 3C 35 bp dsDNA, FIG. 3D 90 bp dsDNA and FIG. 3E 122 bp dsDNA anchored to surface via a flexible PEG linker. The measured heights correspond to tilt angles of 26°, 29°, and 34°, respectively. Histogram of measured heights for FIG. 3F 35 bp dsDNA and FIG. 3G 122 bp dsDNA nonspecifically adsorbed to a silane monolayer. The measured heights indicate that the DNA lies flat on the surface. Errors correspond to standard error of mean.

DISCUSSION AND CONCLUSIONS

In summary, SWAN has an axial resolution that exceeds all previously described single molecule techniques and can be used to localize the z-position of single fluorescent objects with nanometer accuracy and precision. While a total of $5 \times 10^4$ to $10 \times 10^4$ photons were used in the nanosphere experiments to quantify the precision of SWAN, it is important to note that this count corresponds to the total number of photons measured over the 1 s duration of the experiment. This photon budget is merely a factor of 5 to 10 greater than the $8 \times 10^3$ to $2 \times 10^4$ photons collected in each experiment with Cy3 labeled DNA. To estimate the resolution of SWAN using single Cy3 fluorophores, we reduced the total photon budget in FIG. 2D to either $4 \times 10^4$ photons, $2 \times 10^4$ photons, or $8 \times 10^3$ photons by analyzing every 2nd, 4th, or 10th data point. The bead radii determined using this method had a FWHM of 4.3, 5.8, and 6.0 nm, respectively. A future study will experimentally determine the dependency of SWAN precision on photon budget.

We used SWAN to show that dsDNA, grafted at low densities using polymer tethers, are oriented at an average tilt of 30° with respect to the surface, which agrees with calculated tilt angles for freely rotating stiff rods. It is important to note that because of the long measurement time (approximately 1 s per molecule) relative to the time scale for molecular rearrangements, we measure only the average tilt angle adopted by the dsDNA and not its instantaneous orientation. Previous ensemble measurements using densely grafted DNA, measured average tilt angles of 50° and 40° for 21 bp and 50 bp dsDNA[22]. It is likely that the tilt value measured using SWAN is smaller because the low grafting density of dsDNA reduces steric constraints and permits the DNA tether to sample a larger range of conformations. Using SWAN, we also show that dsDNA adsorbed to a positively charged surface lays flat. Finally, a single-stranded G-quadruplex sequence, folds into a structure where its 5' and 3' ends are adjacent to each other.

Errors in SWAN primarily arise from imprecise localization of the AFM tip over the fluorophore, instrumental drift between successive measurements as well as dye photophysics. To quantify these errors, we compared two different measurement strategies. In the first approach, we aligned the AFM tip over a single nanosphere (Bead F) and then measured its radius 100 times by simultaneously recording fluorescence oscillations and excitation laser interference. This measurement yielded a standard deviation in bead radius of 1.6 nm (FIG. 2D). In the second approach, we performed 100 measurements where we sequentially aligned the AFM tip over the nanosphere, measured fluorescence oscillations, and then measured excitation laser interference. The measurement precision using this strategy was lower than the first approach; the standard deviation in bead radius was now 5.4 nm (see Supporting Information, infra, and FIG. 8). We believe that the first strategy reduces instrumental drift by minimizing the time between successive measurements.

It is important to note that other interferometric methods assume that fluorescence interference occurs only at the peak wavelength of the fluorescence spectra[14, 15, 17]. Due to the broad emission spectra of fluorescent dyes, this approximation introduces systematic errors in axial localization. In contrast to these methods, periodic fluorescence oscillations measured in SWAN occur due to standing wave excitation of the fluorophore and not due to fluorescence interference. This improves the localization accuracy of SWAN. Although a small fraction of the fluorescence emitted by a dye will reflect off the AFM tip and interfere with the directly emitted fluorescence, this effect is minimal due to the small radius of curvature of the AFM tip (~10 nm) and the large separation between the tip and surface (≥200 nm). To confirm this, we measured the oscillation period for the fluorescence and excitation laser (Supporting Information, infra, and FIG. 9). Both oscillations have the same period a ($\lambda_{laser}/2n$) confirming that the measured fluorescence oscillations are only due to standing wave excitation.

Unlike other interference-based approaches, SWAN does not require custom optics or specially engineered substrates. This makes the technique easy to use and well suited for biological samples such as lipid membranes, microfibers, protein complexes, and live cells. Moreover, unlike most interference-based techniques, where the interference pattern repeats itself and limits the working range to ~250 nm, the standing wave in SWAN decays with tip-surface distance, which allows successive periods to be distinguished and extends the working distance. SWAN can be easily integrated with other super-resolution and super-accuracy techniques to obtain nanometer resolution along both the lateral and axial directions. Finally, a unique advantage of SWAN is that it can be used to determine the axial position of molecules in single molecule AFM force measurements and in single molecule cut and paste applications for the bottom-up assembly of biological nanostructures[27].

FOOTNOTED REFERENCES

1. Thompson, R. E.; Larson, D. R.; Webb, W. W. Biophys. J. 2002, 82, 2775-2783.
2. Yildiz, A.; Forkey, J. N.; McKinney, S. A.; Ha, T.; Goldman, Y. E.; Selvin, P. R. Science 2003, 300, 2061-2065.
3. Churchman, L. S.; Okten, Z.; Rock, R. S.; Dawson, J. F.; Spudich, J. A. Proc. Natl. Acad. Sci. U.S.A. 2005, 102, 1419-23.
4. Gordon, M. P.; Ha, T.; Selvin, P. R. Proc. Natl. Acad. Sci. U.S.A. 2004, 101, 6462-5.
5. Qu, X.; Wu, D.; Mets, L.; Scherer, N. F. Proc. Natl. Acad. Sci. U.S.A. 2004, 101, 11298-303.
6. Rust, M. J.; Bates, M.; Zhuang, X. W. Nat. Methods 2006, 3, 793-795.
7. Betzig, E.; Patterson, G. H.; Sougrat, R.; Lindwasser, O. W.; Olenych, S.; Bonifacino, J. S.; Davidson, M. W.; Lippincott-Schwartz, J.; Hess, H. F. Science 2006, 313, 1642-1645.
8. Hess, S. T.; Girirajan, T. P.; Mason, M. D. Biophys. J. 2006, 91, 4258-72.
9. Klar, T. A.; Hell, S. W. Opt. Lett. 1999, 24, 954-956.
10. Hell, S. W.; Wichmann, J. Opt. Lett. 1994, 19, 780-782.
11. Huang, B. Nat. Methods 2011, 8, 304-305.
12. Huang, B.; Wang, W.; Bates, M.; Zhuang, X. Science 2008, 319, 810-3.
13. Xu, K.; Babcock, H. P.; Zhuang, X. Nat. Methods 2012, 9, 185-8.
14. Shtengel, G.; Galbraith, J. A.; Galbraith, C. G.; Lippincott-Schwartz, J.; Gillette, J. M.; Manley, S.; Sougrat, R.; Waterman, C. M.; Kanchanawong, P.; Davidson, M. W.; Fetter, R. D.; Hess, H. F. Proc. Natl. Acad. Sci. U.S.A. 2009, 106, 3125-3130.
15. Aquino, D.; Schonle, A.; Geisler, C.; von Middendorff, C.; Wurm, C. A.; Okamura, Y.; Lang, T.; Hell, S. W.; Egner, A. Nat. Methods 2011, 8, 353-U108.
16. Braun, D.; Fromherz, P. Appl. Phys. A 1997, 65, 341-348.
17. Kerssemakers, J.; Howard, J.; Hess, H.; Diez, S. Proc. Natl. Acad. Sci. U.S.A. 2006, 103, 15812-15817.
18. Sivasankar, S.; Chu, S. Nano Lett. 2009, 9, 2120-2124.
19. Ozkumur, E.; Needham, J. W.; Bergstein, D. A.; Gonzalez, R.; Cabodi, M.; Gershoni, J. M.; Goldberg, B. B.; Unlu, M. S. Proc. Natl. Acad. Sci. U.S.A. 2008, 105, 7988-7992.
20. Gray, D. E.; CaseGreen, S. C.; Fell, T. S.; Dobson, P. J.; Southern, E. M. Langmuir 1997, 13, 2833-2842.
21. Wolf, L. K.; Gao, Y.; Georgiadis, R. M. Langmuir 2004, 20, 3357-3361.
22. Moiseev, L.; Unlu, M. S.; Swan, A. K.; Goldberg, B. B.; Cantor, C. R. Proc. Natl. Acad. Sci. U.S.A. 2006, 103, 2623-2628.
23. DeSantis, M. C.; Zareh, S. K.; Li, X. L.; Blankenship, R. E.; Wang, Y. M. Opt. Express 2012, 20, 3057-3065.
24. Smith, F. W.; Feigon, J. Nature 1992, 356, 164-168.
25. Smith, S. B.; Finzi, L.; Bustamante, C. Science 1992, 258, 1122-1126.
26. Bensimon, A.; Simon, A.; Chiffaudel, A.; Croquette, V.; Heslot, F.; Bensimon, D. Science 1994, 265, 2096-2098.
27. Kufer, S. K.; Puchner, E. M.; Gumpp, H.; Liedl, T.; Gaub, H. E. Science 2008, 319, 594-596.

Each of the above-listed footnoted references are incorporated by reference herein.

Supporting Information.

The following information supports the discussion of SWAN above. In particular reference should also be taken to FIGS. 4-9. See also Li Yen, and Sivasankar, S., NANO LETT. 2012, 12, 3731-3735 and supporting material available free of charge at http://pubs.acs.org, each of which is incorporated by reference herein in its entirety.

SWAN Setup (FIG. 4):

In SWAN, a closed-loop, tip-scanning, AFM (Agilent 5500) is mounted on a standard sample scanning, confocal fluorescence microscope. An excitation laser beam (532 nm) was focused to a diffraction-limited spot on a glass cover slip using a 60×, 1.42 N.A., oil-immersion objective (Olympus). The cover slip was functionalized with fluorescent molecules, enclosed in a fluid-cell and mounted on a manual, 2-axes translation stage and a closed loop piezoelectric stage (100 µm×100 µm, Physik Instrumente) for coarse and fine positioning. A custom-made, low vibration adaptor was used to mate the AFM to the confocal microscope. The AFM was modified with an 880 nm infrared Super Luminescent Diode (Q-Photonics) to spectrally separate the AFM light source from Cy3 fluorescence. Fluorescence from the sample was collected by the same objective and focused onto the detection face of an Avalanche Photodiode (APD, Micro Photon Devices). A motorized flipper equipped with a band-pass filter and a ND filter was positioned in front of the objective to transmit either Cy3 fluorescence or excitation light to the APD. Alternatively, to reduce data acquisition time, a dichroic beam splitter was used to separate the fluorescence and excitation light and a second APD was used to measure interference of the laser. Custom software written in LabView was used to control the microscope and synchronize AFM tip movement with fluorescence data collection.

FIG. 4. Schematic of SWAN Microscope.

A closed-loop, tip-scanning, AFM is mounted on a home-built, sample scanning, confocal fluorescence microscope. Abbreviations used in the figure: ND, neutral density filter; S, shutter; λ/2, ½ wave plate; PBS, polarizing cube beam splitter; M, mirror; D, dichroic beam splitter; λ/4, ¼ wave plate; F, band pass filter; QPD, Quadrant Photodiode; APD, Avalanche Photodiode. Inset: Two alternate detection schemes were used. (a) For simultaneous measurements of fluorescence intensity and excitation laser interference, two APDs were used. A dichroic beamsplitter separated the excitation laser from the fluorescence emission. (b) For sequential measurements of fluorescence intensity and excitation laser interference, a motorized flipper equipped with a band-pass filter and a ND filter was used to transmit either Cy3 fluorescence or excitation light to the APD.

Data Collection (FIG. 5):

Non-fluorescent, silicon AFM cantilevers (Nanoworld, Arrow Cantilevers, Spring Constant 2.8 N/m) were used in the SWAN experiments. First, an image of the AFM tip was obtained by scanning the tip over the focused laser beam and recording light reflected off the tip; the tip position was determined from the centroid of its image. Then, a fluorescence image of the sample was collected by moving the piezoelectric stage. The position of the beads/molecules was determined by fitting their fluorescence to a 2D Gaussian function; each bead/molecule could then be positioned at the center of the focused laser beam. Using this strategy, the center of the focused confocal laser beam, fluorescent molecule and AFM tip was aligned along the microscope's optical axis.

After that, the AFM tip was translated in the axial direction from 200 nm to 1200 nm, while monitoring fluorescence emitted by the beads/molecule positioned under the tip. Since the AFM tip does not make contact with the surface, the absolute tip-surface distance was not known. We corrected for this using two strategies. First, we measured the z-position of the coverslip by monitoring the interference of the excitation laser reflected off the coverslip and AFM tip and used it to correct the fluorescence phase difference of the dye. Ideally, the interference data should be described by equation (2) with $Z_{mol}=0$; however, we measured a constant offset in $Z_{mol}$. This is caused by the large size of the diffraction limited, focused, laser beam relative to the sharp AFM tip, variability in the shape of tip and variations in the angle at which the AFM tip is mounted; for the same tip with the same mount, the offset was always constant. Second, we compared the fluorescence phase difference of the dye to a fiduciary marker on the same sample.

FIG. 5. Steps in Typical SWAN Data Collection.

(a) An image of the AFM tip, held at a constant distance of 500 nm above the surface, was obtained by using the APD to measure the light reflected off the AFM tip as it was scanned over the confocal laser beam. The tip position was determined from the centroid of its image. The tip was moved to the center of the focused laser beam and then withdrawn 7 μm away from the surface. Right Panel: Image of AFM tip. The image is not a perfect circle due to the pyramidal shape of the tip. Scale bar=100 nm. (b) The sample containing immobilized fluorescent beads/molecules was scanned across a 10 μm×10 μm region by moving the piezoelectric stage and the fluorescence at each pixel of the scan was collected using the APD. Right Panel: Typical image of DNA (red circle) and fluorescent streptavidin (blue cross), immobilized on surface. Scale bar=1 μm. (c) The location of beads/molecules was calculated by fitting their fluorescence to a 2D Gaussian function; each bead/molecule was then sequentially positioned at the center of the focused laser beam. Right Panel: Image of a single fluorescent molecule fitted to a 2D Gaussian Function. (d) The AFM tip was now translated in the axial direction, while monitoring fluorescence emitted by the beads/molecule positioned under the tip. Right Panel: Fluorescence intensity during tip approach (red) or retraction (blue) from surface and their corresponding fits to equation (2) (thick lines). (e) To determine the absolute tip-surface distance, the z-position of the coverslip was measured by monitoring the interference of the excitation laser reflected off the coverslip and AFM tip. This was used to correct the fluorescence phase difference of the dye. Right Panel: Laser reflection intensity during tip approach (red) or retraction (blue) from surface and corresponding fits to equation (2) (thick lines).

Finite Difference Time Domain (FDTD) Simulations:

FDTD simulations were performed using a commercial software package, FDTD Solutions (Lumercial Solutions Inc.). A 3.2 μm×3.5 μm simulation region was assigned a refractive index of 1.33 to simulate the buffer environment; perfectly matched layers were used as boundary conditions to absorb all waves incident on them with no reflections. A rectangle of 2 μm×0.6 μm with a refractive index of 1.46 was used to mimic the coverslip. An equilateral triangle (1.1 μm×1.1 μm×1.1 μm) with refractive index of 4.2 was used to mimic the silicon AFM tip. A 0.2 μm thick layer around the surface of coverslip and AFM tip was discretized with mesh size of 1.6 nm (Mesh override region) to account for near field effects, other space was discretized using an auto non-uniform mesh with accuracy of 4 (corresponding to mesh size of about 22 nm). A Gaussian laser source with wavelength of 532 nm, propagating towards the tip, was positioned at the surface of the coverslip. The beam had a spot size of 0.5 μm and diverged according to a NA 1.4 thin lens. Time domain simulations were run, mostly more than 30,000 iterations, until an auto-shutoff criterion was reached. Electric field intensity in the frequency domain was obtained by Fourier transform of the simulated time domain fields normalized by Fourier transform of the source pulse. The tip position was changed from 250 nm to 1.3 μm in 13 nm steps (81 simulations).

Measurement of Nanosphere Diameter with AFM (FIGS. 6A-E):

Diameter of Beads F, Beads A and Beads B were measured in air using a tapping-mode AFM. Nanospheres were diluted, adsorbed on freshly cleaved mica and dried at 70° C. for 2 hours. The samples were then imaged with a Multi-mode AFM (Veeco, Calif.) using Si cantilevers (Model: TESPA, Bruker). Image scan speed and feedback parameters were tuned to obtain sharp images. A first-order flattening was performed on every image. Height of beads was determined by subtracting the maximum height of every bead from the average of the surrounding background.

FIGS. 6A-E. AFM Measurement of Nanosphere Diameter.

Figure 6A:
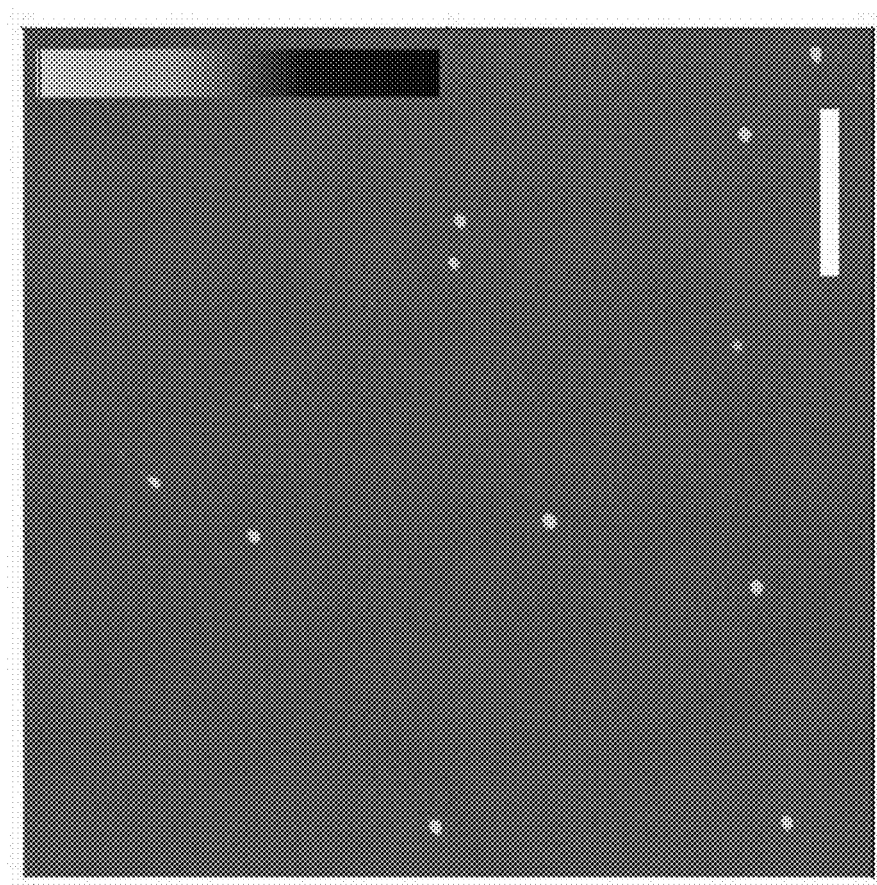
FIGS. 6A-E are an image and graphic charts illustrating AFM measurement of a nanosphere diameter, as can be used in calibration or validation of the SWAN method.
Figure 6E:
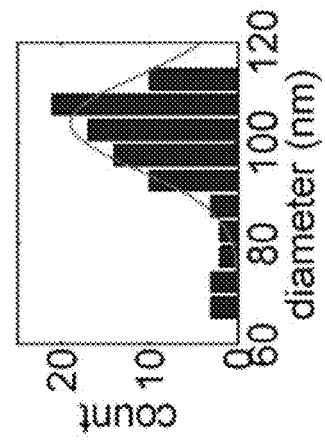
Figure 6B:
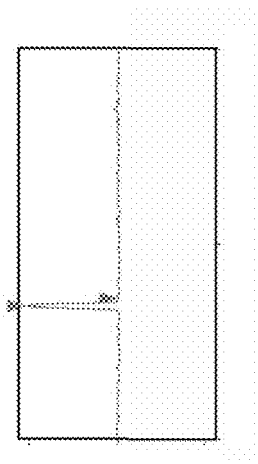
Figure 6D:
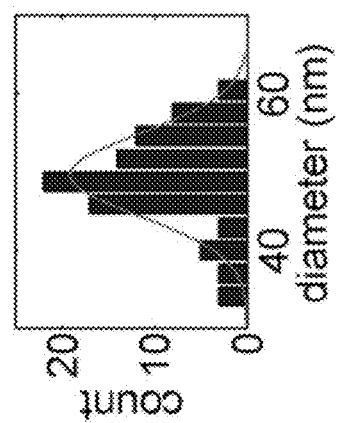
Figure 6C:
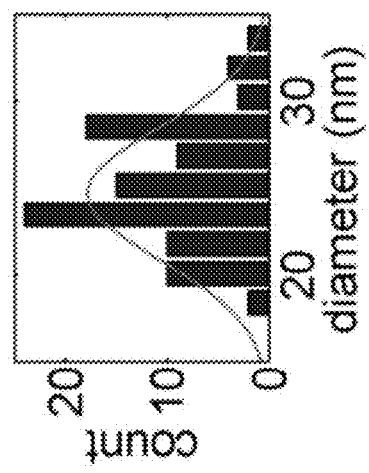

FIG. 6A: Typical AFM topography image of a Bead A sample. The color bar represents height from 0 to 50 nm. FIG. 6B: Topography along the line in (a) shows height (diameter) of a bead. FIG. 6C: Histogram of diameter of 97 Beads F. Gaussian fit has a peak value of 24.7 nm and FWHM of 7.5 nm. Arithmetic average of the nanosphere diameter (mean±SEM) is 25.2±0.4. FIG. 6D: Histogram of diameter of 90 Beads A. Gaussian fit has a peak value of 49.6 nm and FWHM of 10.3 nm. Arithmetic average of the nanosphere diameter (mean±SEM) is 49.0±0.6. FIG. 6E: Histogram of diameter of 85 Beads B. Gaussian fit has a peak value of 104.0 nm and FWHM of 18.0 nm. Arithmetic average of the nanosphere diameter (mean±SEM) is 99.2±1.3.

Estimation of the Average Tilt Angle of dsDNA (FIG. 7):

Since the length of the dsDNA used in our experiments is smaller than the persistence length, we modeled dsDNA of length R as a stiff rod. We assumed that the dsDNA freely rotates in the half space above streptavidin due to its flexible linker. The average height, $\bar{h}$, of the dsDNA can be estimated as:

$$\bar{h} = \frac{\int_0^{\pi/2} h^* 2\pi^* R d\theta}{\int_0^{\pi/2} 2\pi^* R d\theta} = \frac{\int_0^{\pi/2} R\sin(\theta)^* 2\pi R\cos(\theta)^* R d\theta}{\int_0^{\pi/2} 2\pi R\cos(\theta)^* R d\theta} = \frac{2\pi R^3 \int_0^{\pi/2} \sin(\theta)\cos(\theta) d\theta}{2\pi R^2 \int_0^{\pi/2} \cos(\theta) d\theta} = R^* \frac{\frac{1}{2}\sin^2(\theta)\big|_0^{\pi/2}}{\sin(\theta)\big|_0^{\pi/2}} = R/2$$

So the average tilt angle is $\bar{\theta}=\arcsin(\bar{h}/R)=30°$

Figure 7:
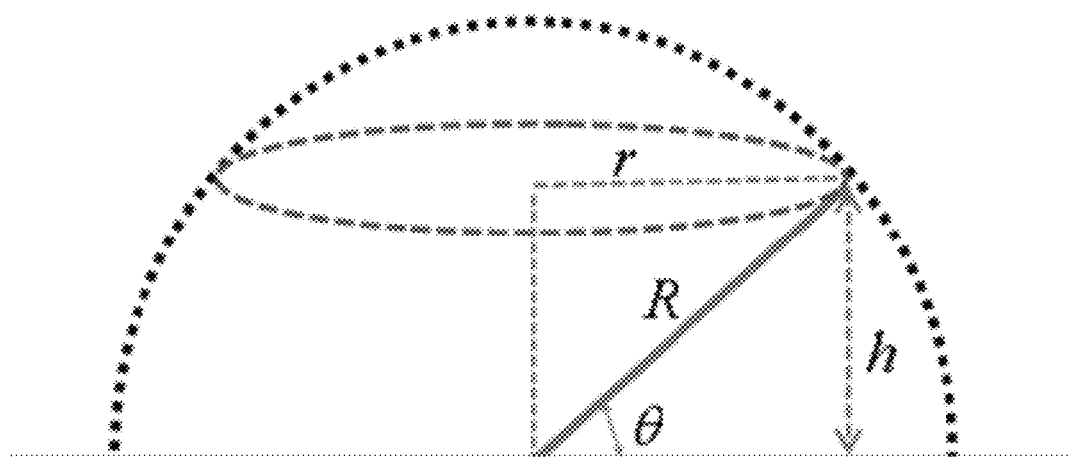
FIG. 7 is a schematic diagram illustrating application of SWAN axial localization to also estimate orientation of an elongated nanostructure.

FIG. 7. Schematic for Calculation of the Average Tilt Angle of a Free Rotating Rod.

Preparation of Fluorescent Nanosphere Sample:

Fluorescent nanospheres (Thermo Scientific) with radii of 12.5 nm (Beads F), 25 nm (Beads A) and 50 nm (Beads B) were adsorbed onto freshly cleaned glass coverslips using 100 mM $CaCl_2$. The nanospheres were pre-mixed and diluted to yield a surface density of approximately 1 bead/10 $\mu m^2$.

Preparation of DNA Sample:

Single strand DNA (35 bases) and three double strand DNA sequences (35 bp, 90 bp, 122 bp) were used to demonstrate single molecule axial localization by SWAN. The DNA molecules (Integrated DNA Technologies) were labeled with a single Cy3 fluorophore at one end and a biotin anchor at the other end. The DNA sequences used are listed below.

35 bases ssDNA (SEQ ID NO: 1):
Cy3-5'-TGG GGT TTT GGG GTT TTG GGG TTT TGG GGA GAT GG-3'-biotin 35 bp dsDNA:
Strand 1 (SEQ ID NO: 1): Cy3-5'-TGG GGT TTT GGG GTT TTG GGG TTT TGG GGA GAT GG-3'-biotin
Strand 2 (SEQ ID NO:2): 5'-CCA TCT CCC CAA AAC CCC AAA ACC CCA AAA CCC CA-3'

90 bp dsDNA:
Strand 1 (SEQ ID NO:3): 5'-CCC AGT TGA GCT GTG AGA ACC CCC TGT GCT TCA GGT TAT AAG ATT CCT CTA GGT AAA GTT GCG CCA CGG ACA ACA TCC GAT AGA ACG GCC-3'-biotin
Strand 2 (SEQ ID NO: 4): 5'-GGC CGT TCT ATC GGA TGT TGT CCG TGG CGC AAC TTT ACC TAG AGG AAT CTT ATA ACC TGA AGC ACA GGG GGT TCT-3 and 5'-CAC AGC TCA ACT GGG-3'-Cy3

122 bp dsDNA:
Strand 1 (SEQ ID NO: 5): 5'-CCC AGT TGA GCT GTG AGA ACC CCC TGT GCT TCA GGT TAT AAG ATT CCT CTA GGT AAA GTT GCG CCA CGG ACA ACA TCC GAT AGA ACG GCC GTC CAA CTG GCG TCA GGT ACA CCT CGC CAC CC-3' Strand 2 (SEQ ID NO: 6): biotin-5-GGG TGG CGA GGT GTA CCT GAC GCC AGT TGG ACG GCC GTT CTA TCG GAT GTT GTC CGT GGC GCA ACT TTA CCT AGA GGA ATC TTA TAA CCT GAA GCA CAG GGG GTT CT-3' and 5'-CAC AGC TCA ACT GGG-3'-Cy3

The DNA was either tethered to a Polyethylene Glycol (PEG) polymer cushion (Laysan Bio Inc.) decorated with non-fluorescent streptavidin (Sigma-Aldrich) or was non-specifically adsorbed to a self-assembled monolayer of positively charged APTES (Sigma-Aldrich). To immobilize the DNA, glass coverslips were first cleaned by heating in a piranha solution (25% $H_2O_2$:75% $H_2SO_4$) at 60° C. for 30 min and then rinsed with deionized water. The coverslips were subsequently sonicated in 1M KOH for 15 min, rinsed with deionized water, and dried using filtered, compressed air. The coverslips were finally incubated in 2% solution of APTES dissolved in Acetone for 30 min, rinsed with Acetone and deionized water, and dried using filtered air. The dsDNA was non-specifically adsorbed to the APTES monolayer. The APTES surface was also incubated with 20 pM fluorescent streptavidin (Invitrogen), for 30 min; the fluorescent streptavidin non-specifically bound to the surface and served as fiduciary markers. Since fluorescent streptavidin has 2 to 3 Alexa Fluor® 555 dyes per protein, it is bright and can be easily distinguished from the DNA molecules.

To tether DNA on PEG linkers, the silanized coverslips were first functionalized with PEG (MW 5000) containing an amine-reactive N-hydroxysuccinimide ester at one end. The silanized coverslips were incubated with 100 mg/ml of a 1:9 stoichiometric mixture of Biotin-PEG and m-PEG, dissolved in $NaHCO_3$ buffer (pH 8.0) for 3 hours. The coverslips were then rinsed with deionized water, dried with filtered compressed air and stored in vacuum. Before an experiment, the coverslip was incubated with 20 pM of fluorescent streptavidin fiduciary markers for 10 min; the surface density of fluorescent streptavidin was ~1 molecule/10 $\mu m^2$. The biotinylated surface was then sequentially incubated with 10 nM of non-fluorescent streptavidin and 20-100 pM DNA. All data was collected in a buffer containing 100 mM Tris (pH 7.5), 2 mM EDTA and 50 mM NaCl.

Figure 8:
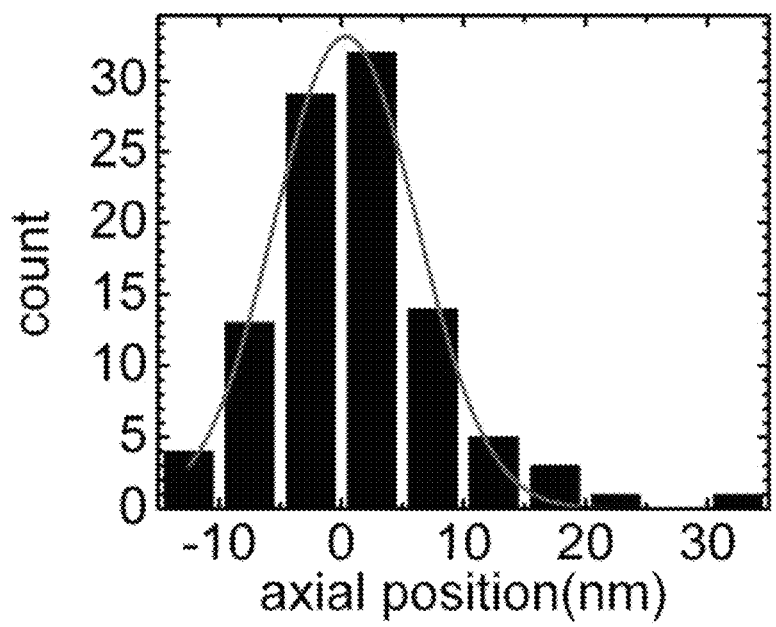
FIG. 8 is a graphic illustration of precision of sequential fluorescence oscillations and then excitation laser interference measurements with SWAN as compared to simultaneous measurements.

FIG. 8. Precision of Sequential Measurements.

The radius of a single nanosphere (Bead F) was measured 100 times. For each measurement, we sequentially aligned the AFM tip over the nanosphere, measured fluorescence oscillations and then measured excitation laser interference. The measurement precision using this strategy was lower than simultaneous measurements due to increased instrumental drift. The standard deviation in the measured bead radius was 5.4 nm.

Figure 9:
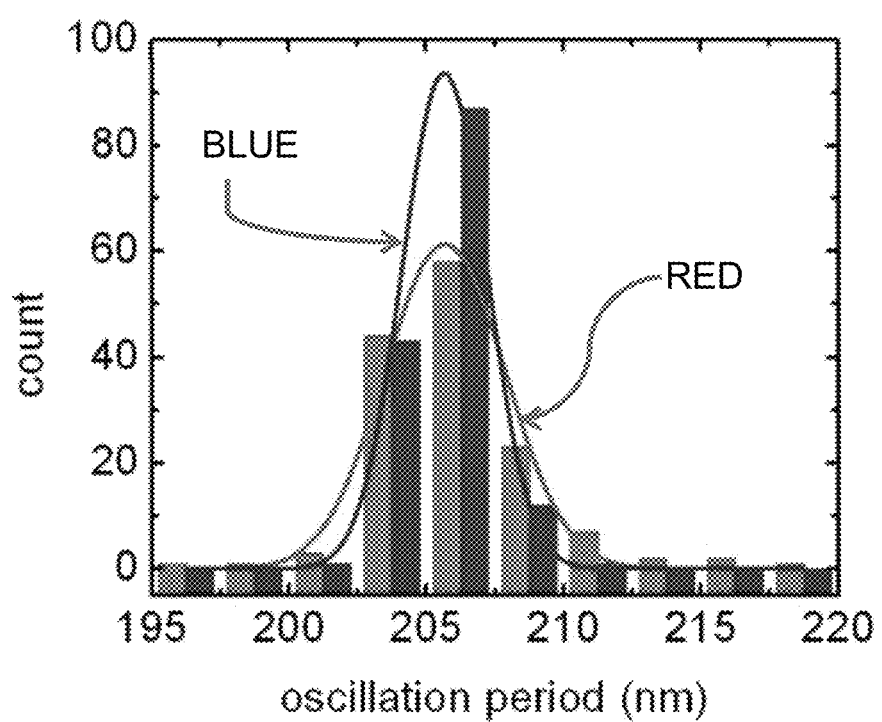
FIG. 9 is a graphic illustration of oscillation period for fluorescence and for the excitation laser relative to SWAN.

FIG. 9. Oscillation Period for Fluorescence and Excitation Laser are Similar.

Distribution of fitted oscillation period (bar) and corresponding Gaussian distribution (solid line) for fluorescence (labeled red) and laser reflection signal (labeled blue). Both oscillations have the same period ($\lambda_{laser}/2n$) confirming that oscillation of fluorescence is only due to standing wave excitation and not due to fluorescence interference.

Positioning AFM Tip Over a Single Molecule.

A critical obstacle in using a sharp AFM probe for combined single molecule AFM-FM measurements is the low probability of interaction between fluorescent molecules on the substrate and the sharp AFM tip. Commercially available AFM tips have a radius of curvature of approximately 10 nm. Similarly a single molecule has a size of approximately 1 nm to 10 nm. When the tip and molecule are visualized, their corresponding image has a size R, that is limited by the wavelength of light: where NA is the numerical aperture of the optical system. With an AFM-FM instrument, images of the tip and molecule have a size of several hundred nanometers. Since the dimensions of both the fluorescent molecules and the radius of curvature of a sharp AFM tip are significantly smaller than these images, the tip cannot be positioned exactly over the fluorescent molecule using diffraction limited optics. This hurdle can be overcome by developing a technology to accurately position the AFM tip over a fluorescent molecule.

Our invention allows the immobilized fluorescent molecule and the AFM tip to be precisely aligned in registry at the center of the confocal microscope laser beam. To locate the AFM tip over a fluorescent molecule we use the following steps:

1. We image the AFM tip and the confocal microscope laser beam using the microscope eyepiece as well as a CCD camera. We then use a manual micrometer stage to coarsely align the AFM tip over the laser beam.
2. We use a closed loop piezoelectric stage (henceforth referred to as piezo-1) to position the AFM tip ~500 nm above the sample surface and again use the manual micrometer stage to move AFM tip to the laser beam.
3. We then scan the AFM tip over the laser beam using piezo-1 and use an avalanche photo diode (APD) to measure the light reflected off the AFM tip. The reflected light is measured at each position of the AFM tip to obtain its image using a home-built LabView program. The AFM tip looks like a round circle in the image (see FIG. 14A—top right image). The center of the tip is located by calculating the centroid of the optical intensity and moving tip to this position with nm precision using piezo-1.
4. With the AFM tip still positioned ~500 nm away from surface, the sample is scanned over the laser beam using a second piezoelectric stage (henceforth referred to as piezo-2) to obtain a fluorescence image of the molecules using our home-built LabView program. Each individual molecule is either identified manually using the computer mouse or detected automatically. Coordinates of the molecule are recorded.
5. Finally, the individual molecules are brought within the laser beam one at a time using piezo-2. The molecules are scanned over the laser beam using piezo-2 (1 um×1 um scan size) to record their image. This image is fitted to a 2D Gaussian function and the location of its peak is calculated. Depending on number of photons collected, the peak position can be located with nanometer accuracy.
6. Using piezo-1, the AFM tip is then used to press or stretch the molecule while recording corresponding changes in fluorescence. A trigger signal indicating start of AFM tip movement is sent to APD (avalanche photo diodes) to synchronize the recording of fluorescence time traces.

We repeat these steps with every fluorescent molecule.

Additional Illustrations of Principles With particular reference to FIGS. 10-22, an additional discussion of principles according to aspects of the present application are diagrammatically and pictorially illustrated.

Motivation.

The benefits and advances made possible by fluorescence microscopy are well documented. See for example the references footnoted previously. Its application to components or processes in living cells, tissues and whole organisms is one of those benefits. Substantial activity in this field of technology continues. However, disadvantages regarding both lateral and axial resolution and optical microscopy remain. See, for example, Huang et al., Annu. Rev. Biochem., Huang, et al. Annu Rev Biochem. 2009. 78: 993-1016. Super resolution fluorescence microscopy (2009), incorporated by reference herein.

One technique at improving lateral accuracy is the previously mentioned FIONA. See footnoted reference 2 for details. Attempts at improvement down to 50-20 nm axial resolution are reported. See footnoted reference 12. Complexity, cost, and other factors leave room for improvement, including additional resolution potential. Examples of applications for such improved axial resolution are described at such publications as Kelly Rae Chi et al., Science, Kelly Rae Chi, NATURE, 2009: Vol. 6, No. 1, January 2009, Super-resolution microscopy: breaking the limit (2009), incorporated by reference herein.

Illustrated Principle of SWAN and Exemplary Setup.

Figure 10:
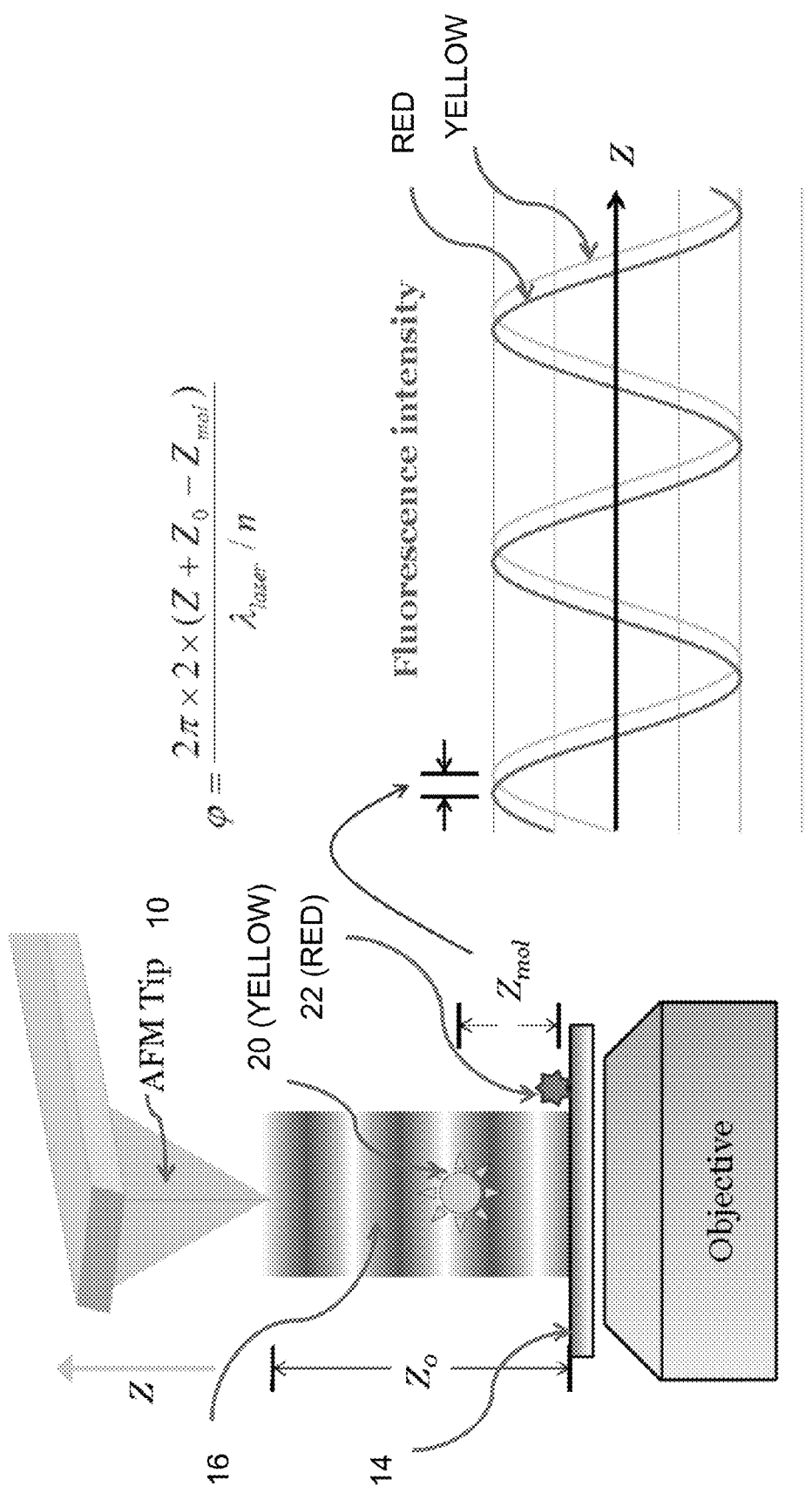
FIG. 10 is a diagrammatic illustration of a methodology according to aspects of the present invention.

FIGS. 10-14B give additional illustration of the general methodology and principles according to the present invention. FIG. 10 illustrates the basic equation and concept of how a phase offset or difference in the measured intensity signal of fluorescence between a fiduciary marker and an object of interest in a standing wave set up between the sample surface and an AFM tip or reflecting surface allows improved precision and accuracy of localization of the object of interest.

Sensitive sensors, such as APDs (Avalanche Photodiodes), capture the oscillating intensity signal of fluorescence from both the fiduciary and the object of interest. Calibration (see discussion regarding the same both above and below) allows a comparison of those signals (in particular their phases, from which to derive offset axially between the two).

Figures 11A, 11B:
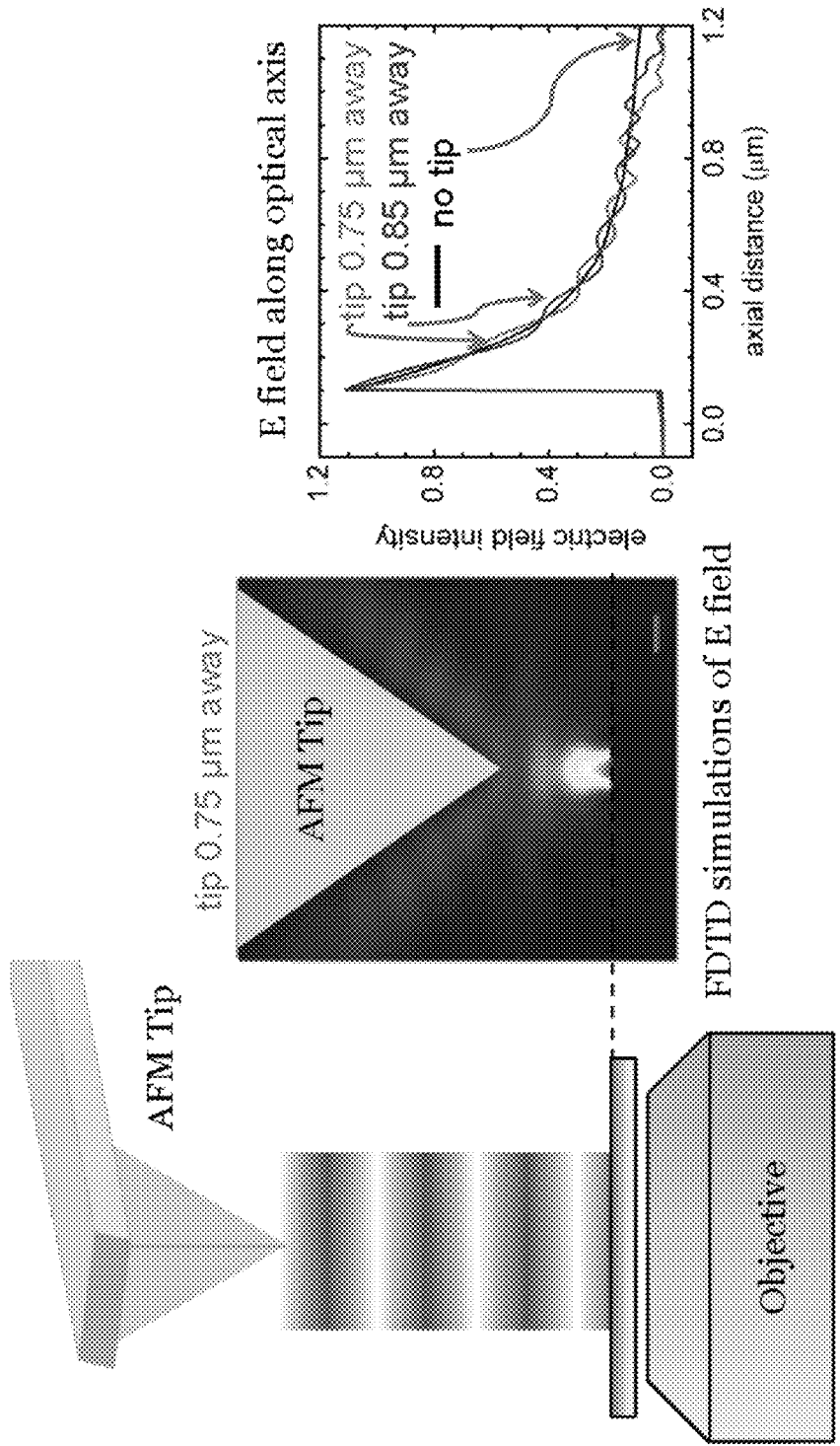
FIGS. 11A and 11B are similar to FIGS. 1A-1C, but add additional illustration.

FIG. 11A illustrates diagrammatically (left side) and with a simulation of E-field (right side) the relationship of an AFM tip to the baseline surface, and how electric field intensity decreases relative to distance. FIG. 11B illustrates the principal of how the phase of a recorded signal changes with distance of the tip relative the baseline surface.

Figure 12B:
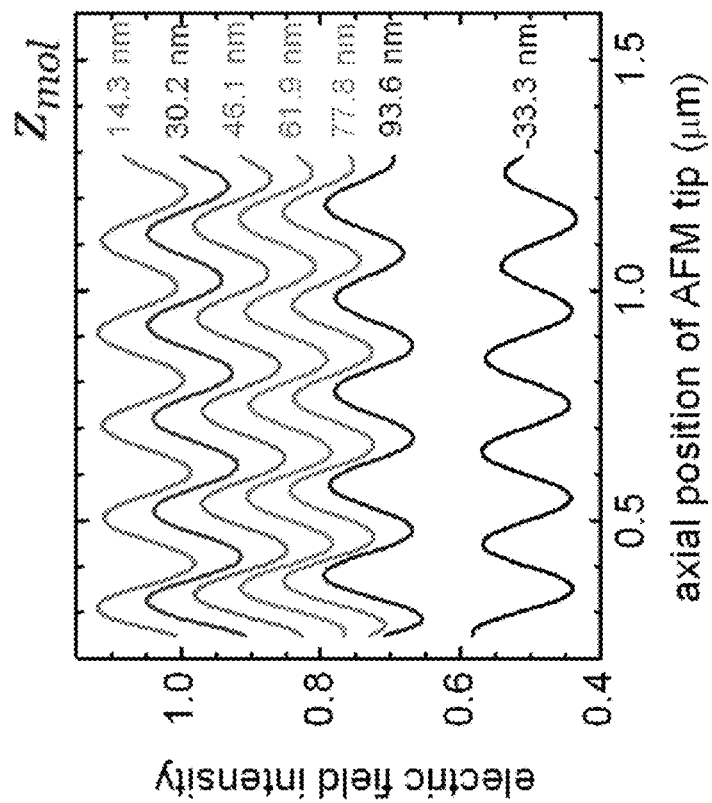
FIGS. 12A and 12B are similar to FIGS. 1A and 1D, but add additional illustration.
Figure 12A:
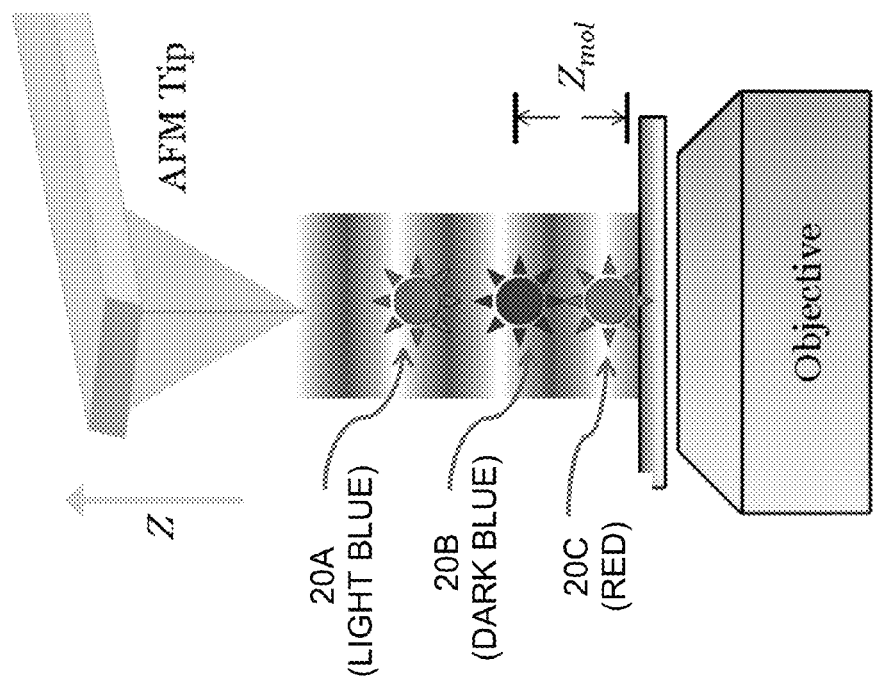

FIG. 12A diagrammatically shows how fluorescing objects 20A, 20B, and 20C at different axial positions between the tip[10] and baseline surface[14] can be correlated to an axial height from the surface ($Z_{mol}$).

Figure 14B:
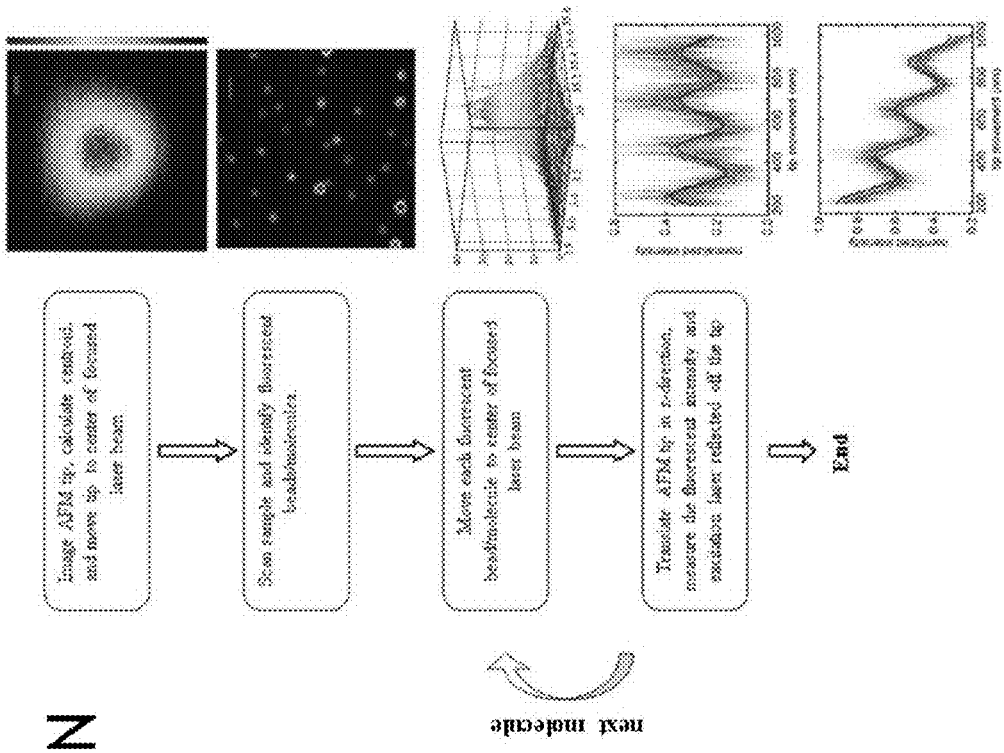
FIGS. 14A and 14B are similar to FIGS. 1A and 5 but show additional illustrations of concepts according to the invention.
Figure 14A:
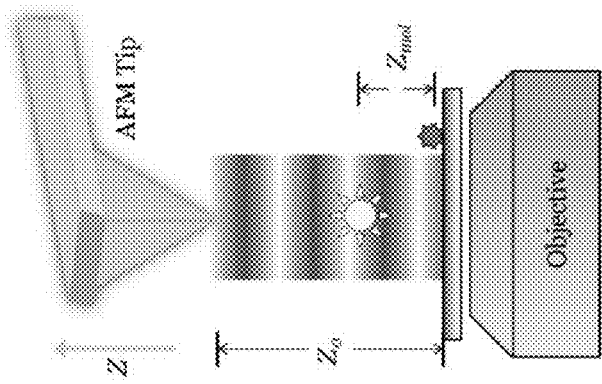
Figure 19:
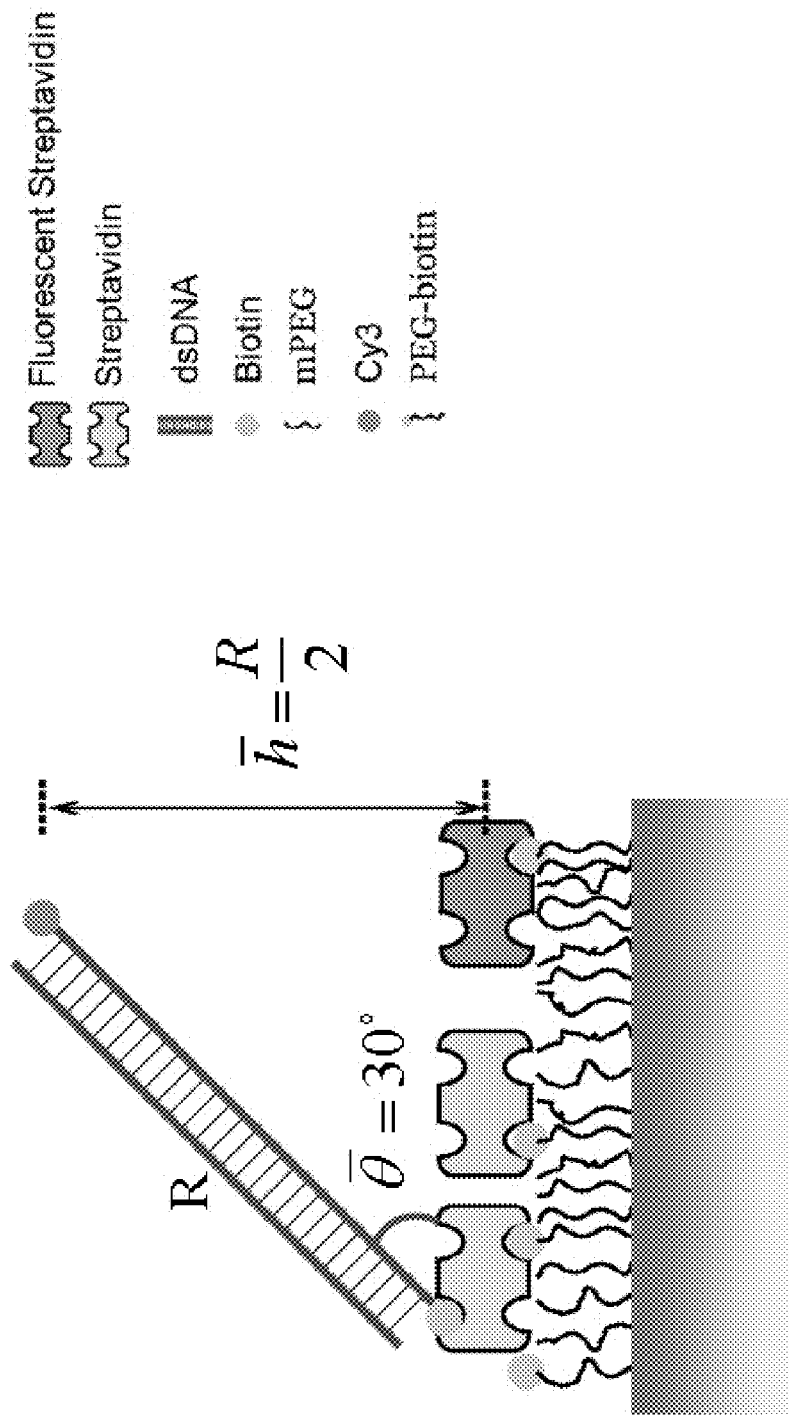
FIG. 19 is a diagrammatic illustration of concepts for using methodology and apparatus of the present invention for estimating orientation of objects.
Figure 20:
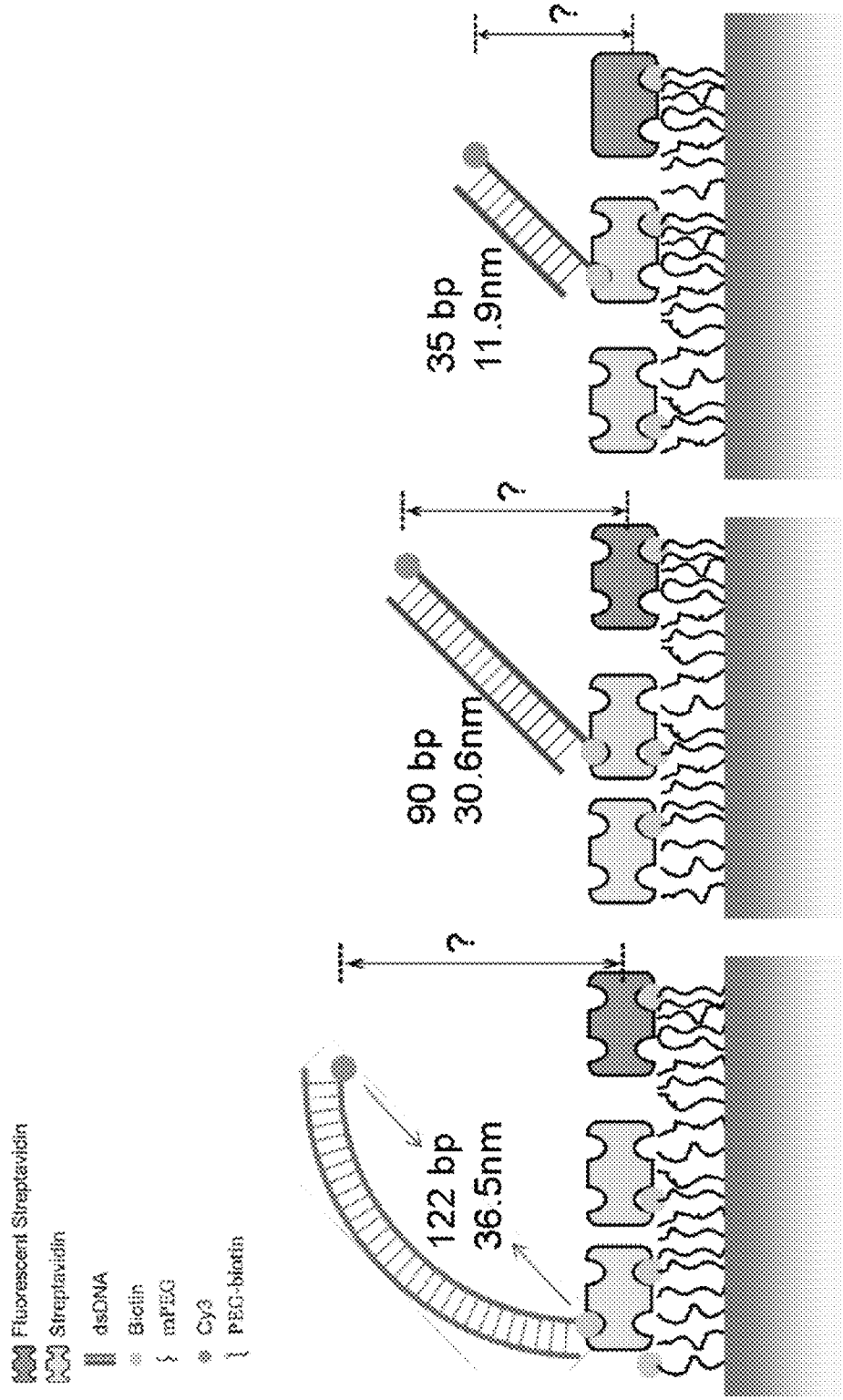
FIG. 20 is similar to FIG. 19 but illustrating concepts related to different size and shape objects.

FIGS. 14A-B illustrate a methodology to derive $Z_{mol}$ for an unknown axial position the object 20 (FIG. 14A). Based on use of lateral localization techniques that are accurate and precise, APD 30 of FIG. 13A records the oscillating fluorescence intensity signal from unknown object 20. APD 32 monitors the excitation intensity reflected back off of tip 10. The right side of FIG. 14B (lower right two graphs of signals) illustrates what APD 30 and APD 32 might measure. Normalization of those oscillating signals can be mathematically conducted and their phases compared to derive $Z_{mol}$ for the particle 20.

Figure 13B:
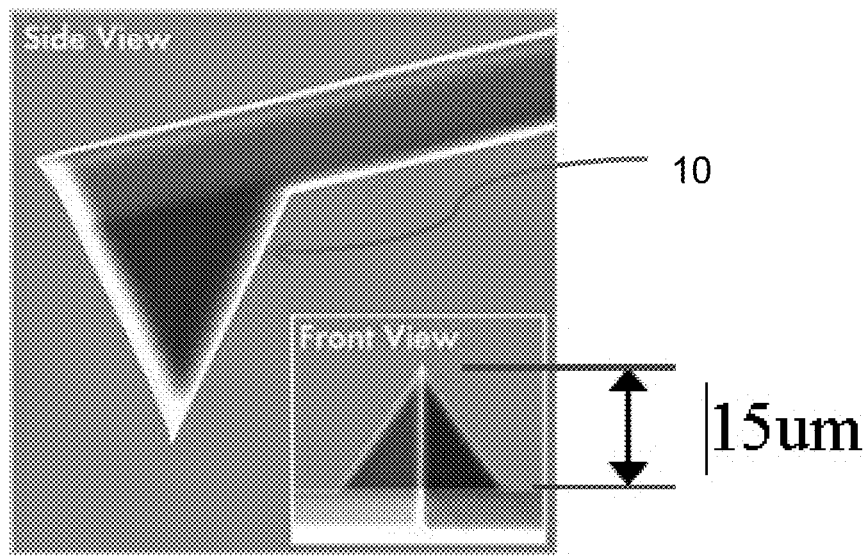
FIGS. 13B and 13C supplement FIG. 13A.
Figure 13C:
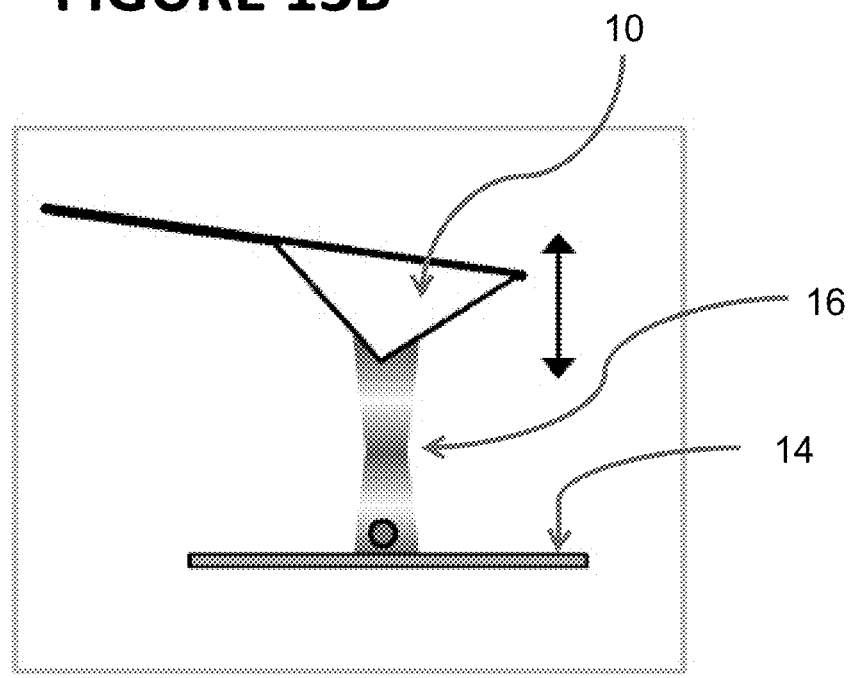

FIGS. 13B-C help illustrate how the AFM tip is precisely moveable in the Z direction and serves as a reflector of the excitation and fluorescing energy.

Calibration of SWAN.

FIGS. 15A-B and 16A-E give additional detail regarding calibration techniques that can be applied. Fiducial marker, of known diameter, as well as at least a plurality of known diameter fluorescing objects (Beads A and B) produce a fluorescence image such as FIG. 15B when excited using the SWAN setup of FIG. 13A. By using the basic algorithm of FIG. 14B (moving the AFM tip laterally located with principles such as shown in FIG. 14B over each of these calibration objects), lateral location can be achieved for each with high accuracy and precision. Using the calibration technique earlier described, a reference for a phase difference between fiducial marker and each of the different size beads A and B can be derived and stored. Expected phase shift for objects at $Z_{mol}$ in between the calibration beads can be extrapolated. The previously described precision of SWAN has been demonstrated to have an axial localization accuracy of sub nanometer (FIGS. 17A-C) and precision of 3.7 nm (see FIGS. 18A-C).

Measuring Single Bio-Molecules by SWAN.

Figure 21:
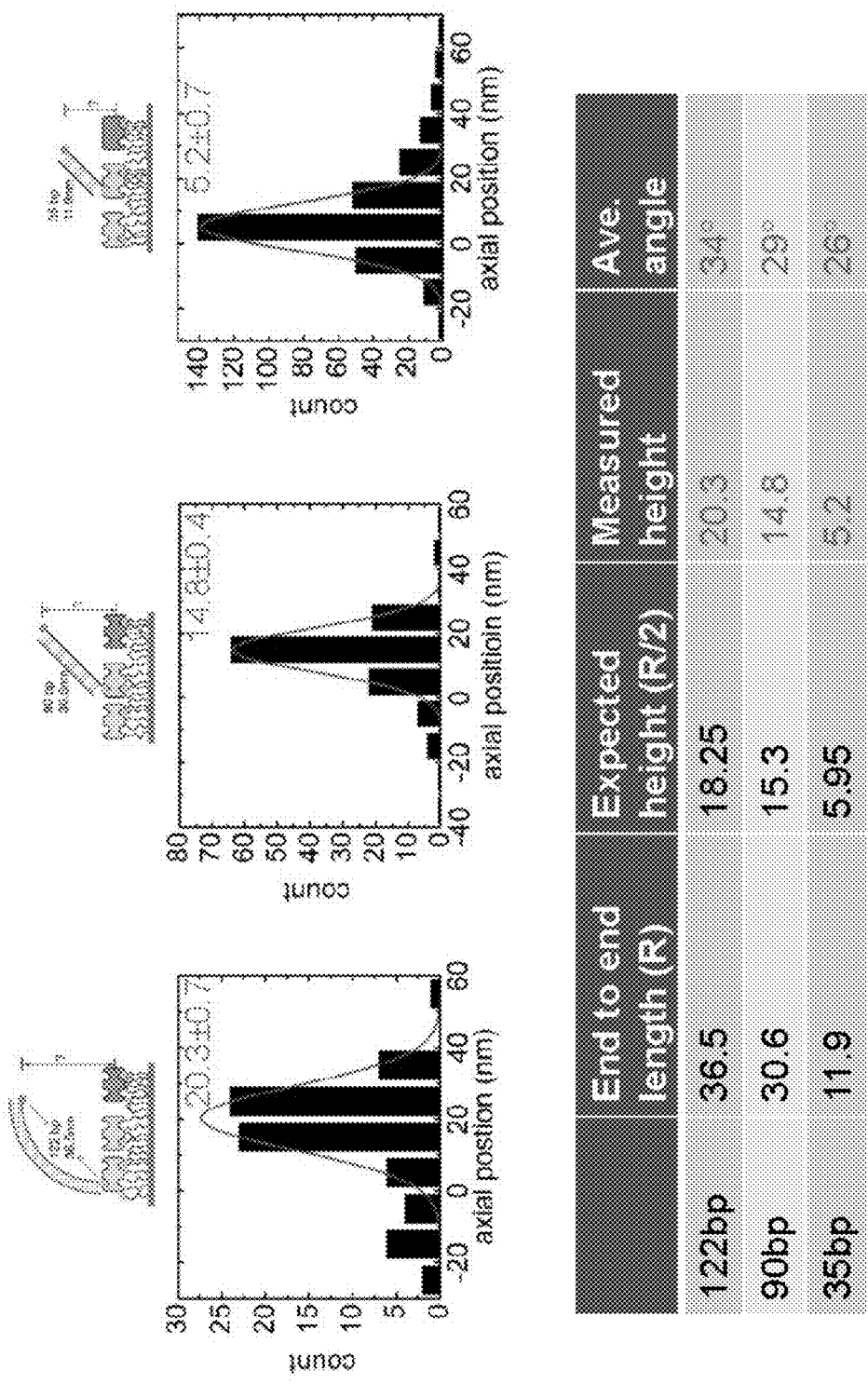
FIG. 21 provides measurement details relative to FIG. 20 using concepts of the present invention.
Figure 22:
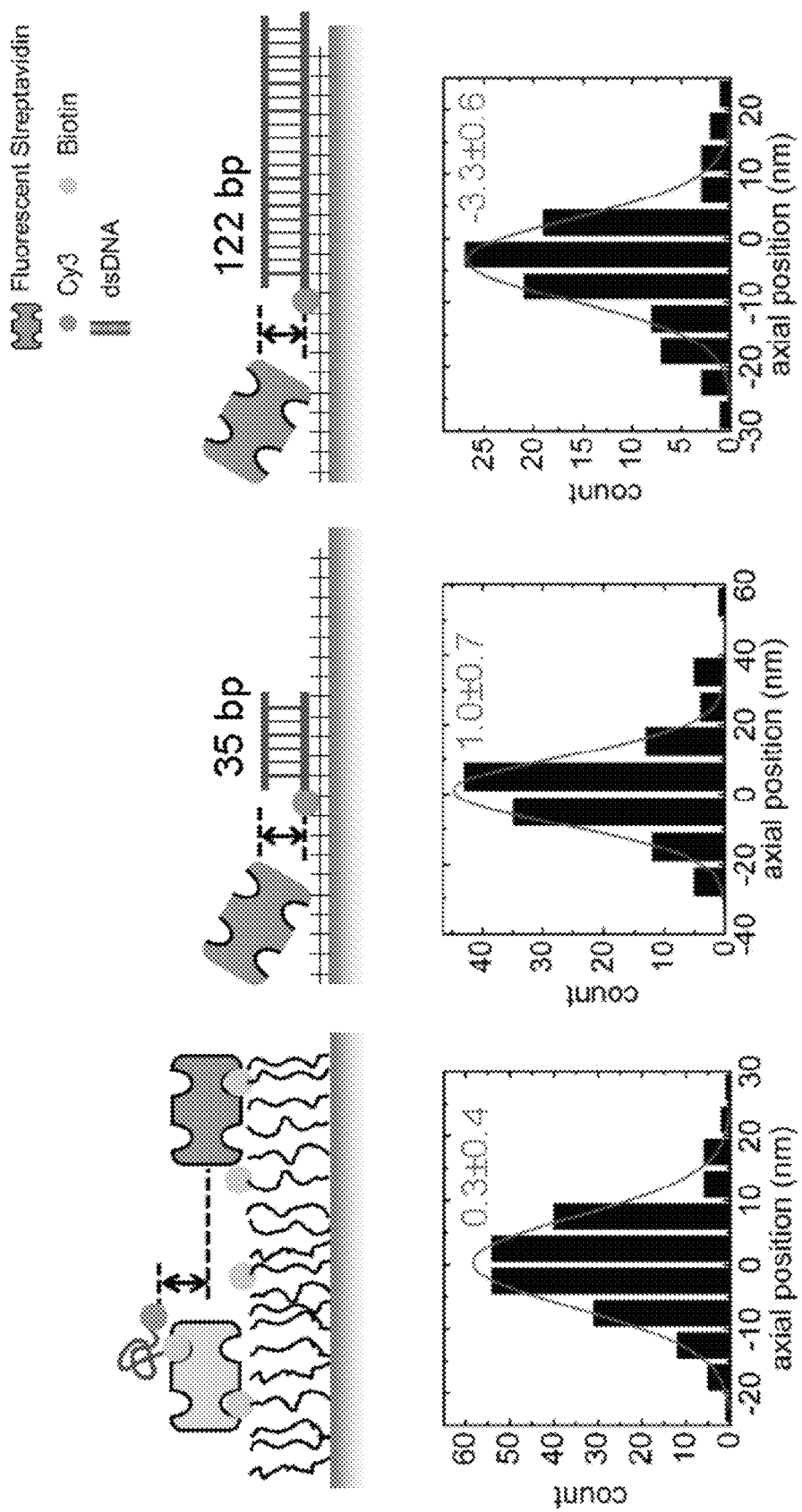
FIG. 22 is another example of measurement concepts for axial height of objects.
Figure 23:
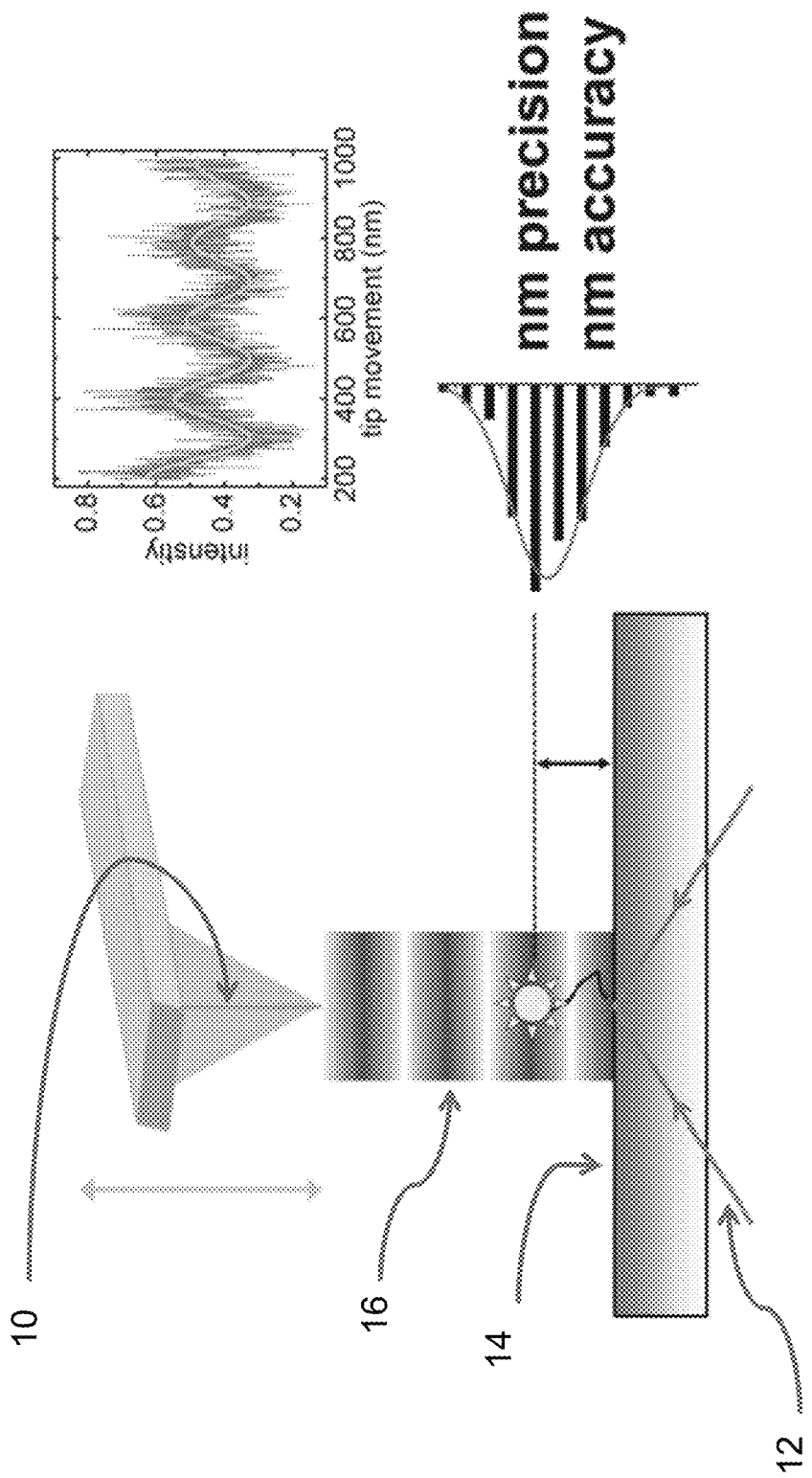
FIG. 23 is a high level diagram illustrating the basic principle according to the present invention.
Figure 24:
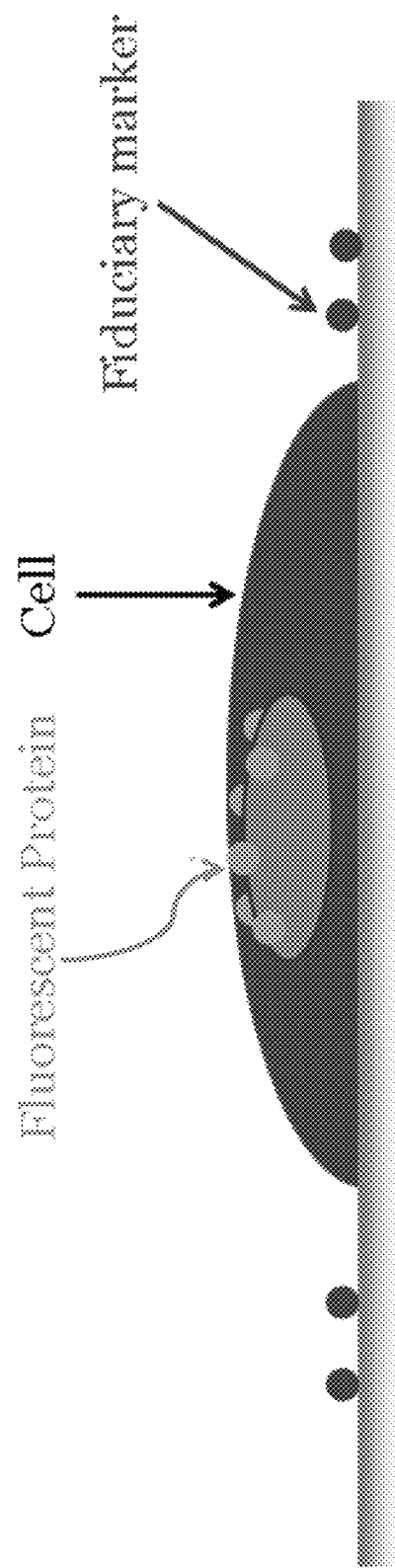
FIGS. 24-27 are highly diagrammatic illustrations of possible applications of the present invention.

FIGS. 19-22 give additional illustrations of how SWAN methodology could be used not only to measure axial position of objects of interest but also orientation, length and height. These particular illustrations relate to biomolecules. Using relatively straightforward geometric relationships, and by placement of fluorescing markers or objects that can be differentiated from one another by wave length of fluorescent emission, lateral localization each with acceptable accuracy plus a priority knowledge of where such different markers exist in bio-molecules, allows estimation of orientation (FIG. 19), length (FIG. 20), and height (FIGS. 21 and 22). As can be seen by the above-additional illustrations and the preceding descriptions and illustrations, SWAN can locate fluorescent objects with 3.7 nm precision and sub-nanometer accuracy in the axial direction. It is capable of detecting single bio-molecules. It is compatible with lateral super-resolution methods. It is compatible with single molecule AFM see FIG. 23.

Example Applications

As can be appreciated by those skilled in the art, the apparatus and methods discussed above can be applied in a variety of ways. Some have been mentioned.

Some of those applications include a variety of applications such as illustrated at FIGS. 24-27.

Using fluorescent protein markers in a single cell relative to fiducial markers, SWAN can be used to locate the fluorescent markers or molecules inside a cell with precision and accuracy. See FIG. 24. Then tracking of those fluorescent molecules with nanometer resolution can proceed. Benefits of the same are widely heralded.

Figure 25:
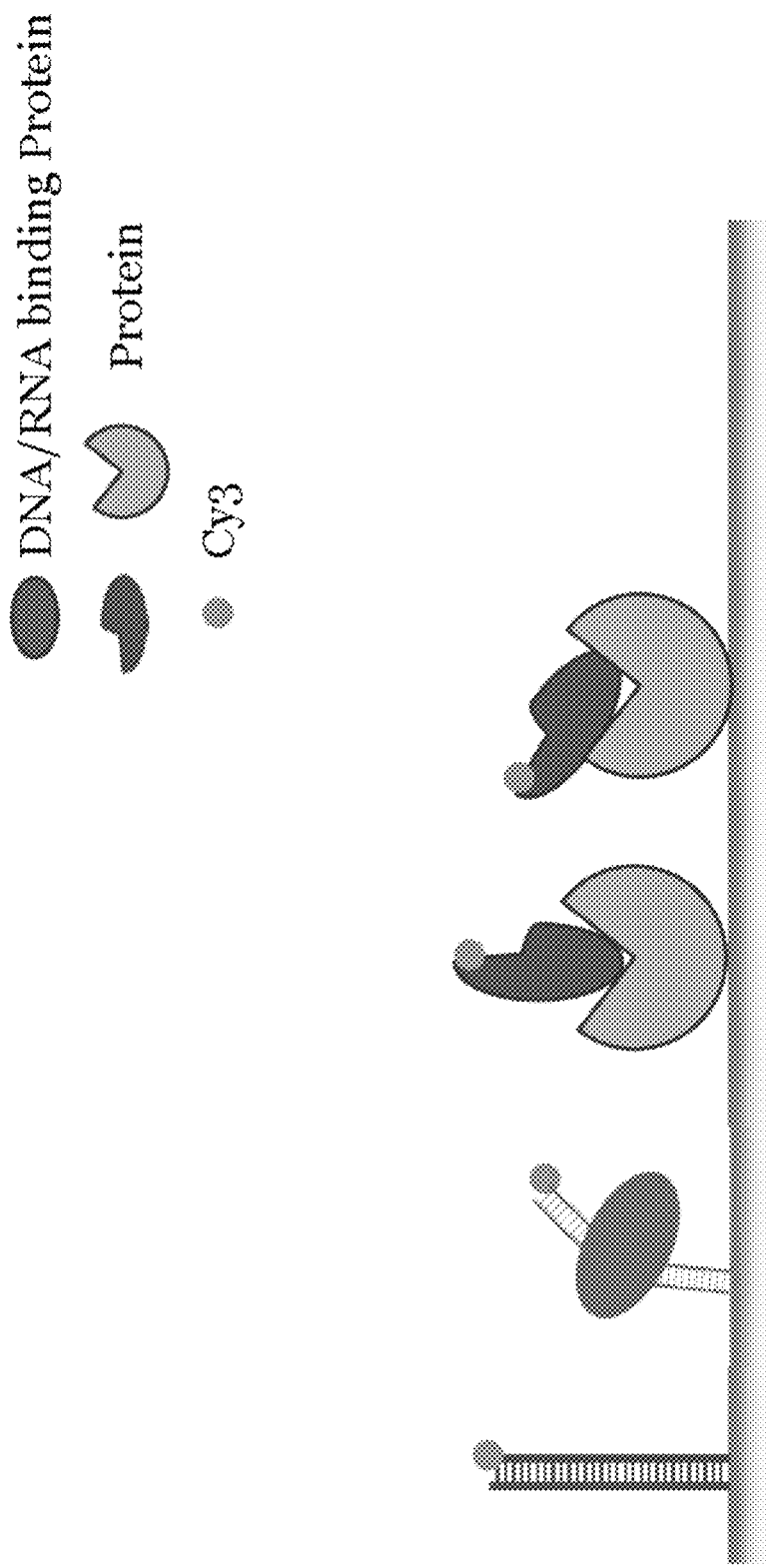

FIG. 25 illustrates similar principles to study protein DNA/RNA interaction, and protein interaction.

Figure 26:
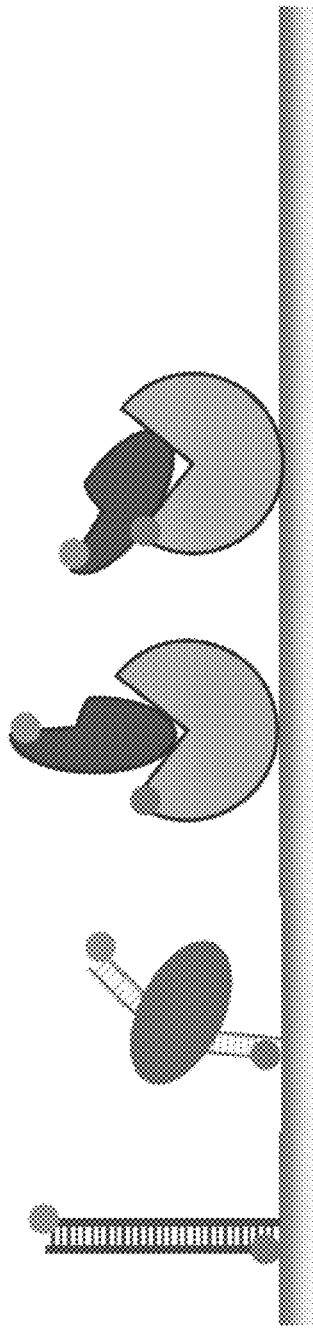

FIG. 26 similarly illustrates potential with plural fluorescing molecules or markers of different or distinguishable fluorescent emission.

Figure 27:
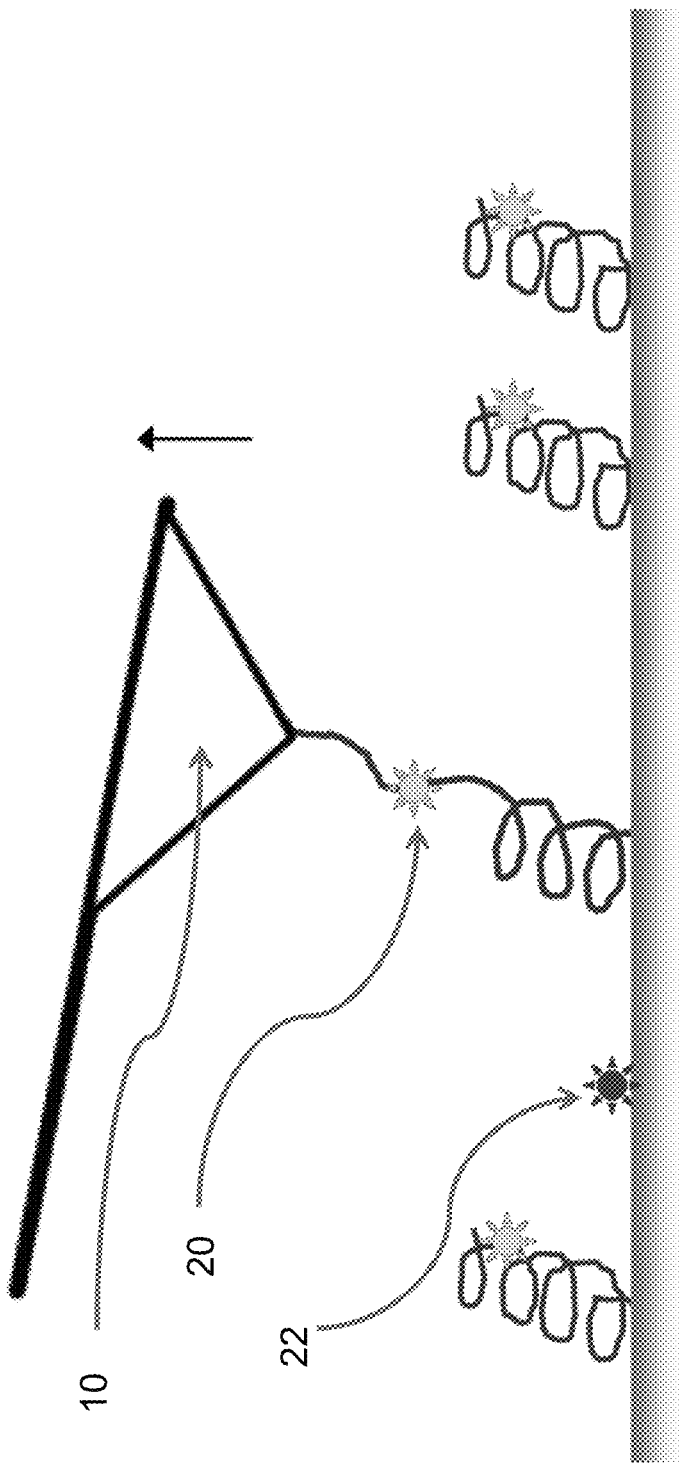

FIG. 27 illustrates potential benefit of simultaneous forced measurement with an AFM tip and SWAN nanometer accuracy and precision axial localization. Combination would predictably yield more reliable AFM force measurements. Utilizing force measurements in studying specimens is well-known. See, e.g., Rief, et al., SCIENCE, Vol. 275, 28 Feb. 1997, pp. 1295-1297, Single Molecule Force Spectroscopy on Polysaccharides by Atomic Force Microscopy, incorporated by reference herein. Of course, other applications are possible utilizing the concepts disclosed herein.

Alternatives & Options

As will be appreciated by those skilled in the art, the invention can take many forms and embodiments. Variations obvious to those skilled in the art will be included within the invention, which is not limited by the specific exemplary embodiments presented herein.

For example, the specific commercial components utilized to form the apparatus can vary according to need or desire. Additionally, the specific samples under investigation can vary.

One alternative is to replace an AFM tip with a scannable mirror or other reflecting surface. As can be appreciated by one skilled in the art, the reflecting surface can be highly specular or at least have sufficient reflectivity to reflect sufficient intensity for measurement according to the methodology of the invention. The reflecting surface can move like an AFM tip. The system would be able to tune the separation resolution between the reflecting surface and reference surface to below the wavelength of light. It is also to be appreciated that the reflecting surface, in whatever form it takes, can be scanned continuously over an applicable range of heights from the reference (e.g., the microscope substrate, or some other surface). This could be a continuous scan with continuous data gathering. Alternatively, the reflecting surface could be moved to discrete positions at different heights from the reference substrate or surface. It could be at uniformly spaced heights or not. Data could be gathered at each discrete height. Of course, a combination of scanning and discrete positions is also possible. As can be further appreciated, depending on the context, movement of the reflecting surface is described as along a Z-axis, an optical axis, or relative to axial location.

The methodology can be applied to a variety of fluorescent microscope types. Examples include, but are not limited necessarily to confocal, wide-field, total internal reflection fluorescent (TIRF), multiphoton, and epi-illumination.

As indicated above, a fluorescent nanoscale object for the methodology can include, but is not limited to, nanoscale structures or a molecule, or plural molecules. The fluorescing object can be measured alone, or in correspondence with other nanoscale or larger objects, structures, or molecules. Some examples are given above. Fiducial markers may or may not be used. They may or may not be fluorescent. The reference surface (e.g., microscope substrate) could be the reference itself.

The detector(s) are shown as APD(s). Others are possible including but not limited to CCD(s).

An example of lateral localization can be also found at co-pending U.S. Ser. No. 13/569,927 filed Aug. 8, 2012 to Sivasankar and Li, incorporated by reference herein.

As can further be appreciated by those skilled in the art, the methodologies could be applied with or without fiducial markers. For example, the reference or sample surface itself could be used as a reference relative to Z or optical axis localization as its Z-axis position would be known or derivable. Other references are possible. Furthermore, the reference relative to which Z-axis height can be measured can be calculated, derived, or achieved by calibration techniques.

The invention claimed is:

1. A method of determining Z-axis position of a fluorescent nanoscale object with nanometer precision and accuracy relative to a reference surface defined by X- and Y-axes comprising:
   a. generating a standing wave excitation pattern between a reflecting surface and the reference surface along the Z-axis with a focused excitation light source selected to excite fluorescence from the object and a reflection of the excitation source along the same Z-axis;
   b. placing the object in the standing wave to generate an excited fluorescence having an intensity that oscillates proportionally to the standing wave;
   c. recording the oscillating intensity and phase of the excited fluorescence while varying distance of the reflecting surface from the object along the Z-axis; and
   d. deriving position of the object along the Z-axis by comparing the phase of the recorded excited fluorescence to a reference.

2. The method of claim 1 wherein the object is or is associated with:
   a. a single molecule;
   b. a lipid membrane;
   c. a microfiber;
   d. a nanostructure;
   e. a protein complex; or
   f. a live cell.

3. The method of claim 1 used for:
   a. localizing molecules with high accuracy;
   b. measuring distances between molecules with high resolution;
   c. estimating orientation of elongated nanoscale structures such as DNA;
   d. single molecule AFM force measurements;
   e. single molecule cut and paste applications; or
   f. three dimensional super-resolution fluorescence microscopy.

4. The method of claim 1 wherein the reflecting surface, focused excitation source, and object are aligned along the optical axis by:
   a. centering the reflecting surface in the excitation light source by:
      i. scanning the excitation source over the reflecting surface;
      ii. recording reflected light from the reflecting surface to image the reflecting surface;
      iii. calculating centroid of the image, and
      iv. moving the reflecting surface to center the calculated centroid in the focused excitation source, and
   b. placing the object in the standing wave by:
      i. scanning the sample surface with the excitation source to fluoresce at least the object;
      ii. imaging the fluorescence;
      iii. fitting the fluorescence to a two-dimensional Gaussian function to estimate center of the object; and
      iv. moving the object to the center of the focused excitation source;
   c. so that the reflecting surface and focused excitation source are aligned along the optical axis and the object is aligned along the optical axis.

5. The method of claim 1 wherein the reference comprises recording excited fluorescence of a plurality of fluorescent reference objects of known and different sizes while on the reference surface and in the standing wave.

6. The method of claim 1 wherein the reference comprises recording intensity of the excitation light source.

7. The method of claim 1 wherein the reference comprises recording excited fluorescence of a fluorescent fiduciary marker while on the reference surface and in the standing wave.

8. The method of claim 1 wherein the object is positioned at one end of an elongated nanostructure of known length and the other end of the elongated nanostructure is fixed relative the reference surface, further comprising estimating orientation of the elongated nanostructure relative the reference surface by;
   a. comparing the derived Z-axis position of the object at the one end and the known length, of the elongated nanostructure;
   b. assuming any substantial offset in the comparison is an oblique orientation of the elongated nanostructure relative the reference surface.

9. The method of claim 8 further comprising calculating an orientation angle of the elongated nanostructure relative to the X-Y plane.

10. The method of claim 1 wherein the Z-axis position comprises the optical axis position relative a fluorescent microscope setup.

11. The method of claim 1 wherein the reflecting surface comprises an AFM tip, a mirror, or a component with at least some reflectivity.

12. The method of claim 1 wherein the reference comprises a fiducial marker or the reference surface.

13. The method of claim 1 wherein the varying distance of a reflecting surface comprises continuous scanning or discrete Z-axis positions.

14. The method of claim 1 wherein the object comprises a nanoscale structure or one or more single molecules.

15. The method of claim 1 used in determining Z-axis position of plural fluorescent objects of a sample.

16. A method of imaging axial location of a single fluorescent nanoscale object with sub-nanometer accuracy and nanometer precision comprising:
   a. exciting fluorescence in the object by placing the object in a standing wave generated by positioning a reflecting surface over a focused laser excitation laser beam; and
   b. determining axial position from phase of the emission intensity of the fluorescence, wherein the step of determining comprises comparing the phase of the emission intensity of one or more calibration references.

17. A system for determining optical axis position with nanometer precision and accuracy of a fluorescent nanoscale object relative to a reference surface comprising:
   a. a fluorescence microscope including an optical axis, a sample surface moveable relative the optical axis, a focused excitation light source along the optical axis, and a detector along the optical axis adapted to collect light intensity information from events occurring at or along the optical axis as a function of time;
   b. a reflecting surface that can be adjusted relative to the sample surface, including along the optical axis;
   c. a processor including programming to:
      i. align the reflecting surface and operate the excitation source to reflect at least partially from the reflecting surface and create a standing wave excitation pattern of incident and reflected excitation light energy;
      ii. estimate position of a fluorescent nanoscale object along the optical axis relative the sample surface by:
         1. placing the object in the standing wave;
         2. deriving phase of fluorescence from the object excited by the standing wave;
         3. comparing phase of the recorded fluorescence to a reference; and 4. assigning axial position of the object relative the optical axis based on the comparison.

18. The system of claim 17 wherein the fluorescence microscope comprises a confocal, wide field, TIRF, multiphoton, or epi-illumination fluorescence microscope.

19. The system of claim 17 wherein the reflecting surface comprises an AFM tip.

20. The system of claim 7 wherein the reflecting surface comprises a mirror.

21. The system of claim 17 further comprising using a fiducial marker as the reference.

22. The system of claim 21 wherein the object comprises one or more fluorescent protein markers in a single cell.

23. The system of claim 21 further comprising a sample having plural molecules or markers of different or distinguishable fluorescent emission.

24. The system of claim 19 further comprising operating the AFM tip in either tapping mode or for force measurements.

* * * * *

UNITED STATES PATENT AND TRADEMARK OFFICE
CERTIFICATE OF CORRECTION

| | |
|---|---|
| PATENT NO. | : 9,103,784 B1 |
| APPLICATION NO. | : 14/081522 |
| DATED | : August 11, 2015 |
| INVENTOR(S) | : Sanjeevi Sivasankar, SuZhou Hui Li and Chi-Fu Yen |

It is certified that error appears in the above-identified patent and that said Letters Patent is hereby corrected as shown below:

Claims

Column 24, Claim 8, line 12:

Delete the "," after the word length

Signed and Sealed this
Fifteenth Day of March, 2016

Michelle K. Lee
*Director of the United States Patent and Trademark Office*

SEQUENCE LISTING

<160> NUMBER OF SEQ ID NOS: 6

<210> SEQ ID NO 1
<211> LENGTH: 35
<212> TYPE: DNA
<213> ORGANISM: Artificial Sequence
<220> FEATURE:
<223> OTHER INFORMATION: Exemplary single strand DNA for demonstration
      of single molecule axial localization by SWAN.

<400> SEQUENCE: 1
tggggttttg gggttttggg gttttgggga gatgg                              35

```
<210> SEQ ID NO 2
<211> LENGTH: 35
<212> TYPE: DNA
<213> ORGANISM: Artificial Sequence
<220> FEATURE:
<223> OTHER INFORMATION: Exemplary double stranded DNA for demonstration
      of single molecule axial localization by SWAN

<400> SEQUENCE: 2
ccatctcccc aaaacccaa aaccccaaaa cccca                                  35

<210> SEQ ID NO 3
<211> LENGTH: 90
<212> TYPE: DNA
<213> ORGANISM: Artificial Sequence
<220> FEATURE:
<223> OTHER INFORMATION: Exemplary double stranded DNA for demonstration
      of single molecule axial localization by SWAN

<400> SEQUENCE: 3
cccagttgag ctgtgagaac cccctgtgct tcaggttata agattcctct aggtaaagtt      60
gcgccacgga caacatccga tagaacggcc                                       90

<210> SEQ ID NO 4
<211> LENGTH: 90
<212> TYPE: DNA
<213> ORGANISM: Artificial Sequence
<220> FEATURE:
<223> OTHER INFORMATION: Exemplary double strand DNA for demonstration
      of single molecule axial localization by SWAN

<400> SEQUENCE: 4
ggccgttcta tcggatgttg tccgtggcgc aactttacct agaggaatct tataacctga      60
agcacagggg gttctcacag ctcaactggg                                       90

<210> SEQ ID NO 5
<211> LENGTH: 122
<212> TYPE: DNA
<213> ORGANISM: Artificial Sequence
<220> FEATURE:
<223> OTHER INFORMATION: Exemplary double strand DNA for demonstration
      of single molecule axial localization by SWAN

<400> SEQUENCE: 5
cccagttgag ctgtgagaac cccctgtgct tcaggttata agattcctct aggtaaagtt      60
gcgccacgga caacatccga tagaacggcc gtccaactgg cgtcaggtac acctcgccac     120
cc                                                                    122

<210> SEQ ID NO 6
<211> LENGTH: 122
<212> TYPE: DNA
<213> ORGANISM: Artificial Sequence
<220> FEATURE:
<223> OTHER INFORMATION: Exemplary double strand DNA for demonstration
      of single molecule axial localization by SWAN

<400> SEQUENCE: 6
gggtggcgag gtgtacctga cgccagttgg acggccgttc tatcggatgt tgtccgtggc      60
gcaactttac ctagaggaat cttataacct gaagcacagg gggttctcac agctcaactg     120
gg                                                                    122
```